United States Patent
Tenne et al.

(10) Patent No.: US 11,446,413 B2
(45) Date of Patent: Sep. 20, 2022

(54) ATTENUATION OF ENCRUSTATION OF MEDICAL DEVICES USING COATINGS OF INORGANIC FULLERENE-LIKE NANOPARTICLES

(71) Applicants: YEDA RESEARCH AND DEVELOPMENT CO. LTD., Rehovot (IL); MOR RESEARCH APPLICATIONS LTD., Tel Aviv (IL)

(72) Inventors: Reshef Tenne, Rehovot (IL); David Zbaida, Rehovot (IL); Racheli Ron, Rehovot (IL); Ilan Kafka, Rehovot (IL); Ilan Leibovitch, Tel Aviv (IL)

(73) Assignees: YEDA RESEARCH AND DEVELOPMENT CO. LTD., Rehovot (IL); MOR RESEARCH APPLICATIONS LTD., Tel-Aviv (IL)

( * ) Notice: Subject to any disclaimer, the term of this patent is extended or adjusted under 35 U.S.C. 154(b) by 418 days.

(21) Appl. No.: 15/109,822

(22) PCT Filed: Jan. 6, 2015

(86) PCT No.: PCT/IL2015/050021
§ 371 (c)(1),
(2) Date: Jul. 6, 2016

(87) PCT Pub. No.: WO2015/102006
PCT Pub. Date: Jul. 9, 2015

(65) Prior Publication Data
US 2016/0331874 A1 Nov. 17, 2016

Related U.S. Application Data

(60) Provisional application No. 61/923,841, filed on Jan. 6, 2014.

(51) Int. Cl.
| | | |
|---|---|---|
| *A61L 29/14* | (2006.01) | |
| *A61L 31/08* | (2006.01) | |
| *A61L 29/10* | (2006.01) | |
| *A61L 31/14* | (2006.01) | |
| *A61L 29/18* | (2006.01) | |
| *A61L 31/18* | (2006.01) | |

(52) U.S. Cl.
CPC ........... *A61L 31/088* (2013.01); *A61L 29/106* (2013.01); *A61L 29/14* (2013.01); *A61L 29/18* (2013.01); *A61L 31/082* (2013.01); *A61L 31/14* (2013.01); *A61L 31/18* (2013.01); *A61L 2400/12* (2013.01); *A61L 2420/02* (2013.01)

(58) Field of Classification Search
CPC ...... A61L 31/088; A61L 29/106; A61L 31/14; A61L 31/082; A61L 29/14; A61L 2420/02; A61L 2400/12
See application file for complete search history.

(56) References Cited

U.S. PATENT DOCUMENTS

| | | |
|---|---|---|
| 3,936,577 A | 2/1976 | Christini et al. |
| 5,035,618 A | 7/1991 | Katz et al. |
| 5,215,461 A | 6/1993 | Riazi |
| 5,228,230 A | 7/1993 | Vaught |
| 5,232,361 A | 8/1993 | Sachdeva et al. |
| 5,344,457 A | 9/1994 | Pilliar et al. |
| 5,454,716 A | 10/1995 | Banerjee et al. |
| 5,868,570 A | 2/1999 | Hickok et al. |
| 5,877,243 A | 3/1999 | Sarangapani |
| 5,958,358 A | 9/1999 | Tenne et al. |
| 6,164,831 A | 12/2000 | Matsui et al. |
| 6,299,438 B1 | 10/2001 | Sahagian et al. |
| 6,409,506 B1 | 6/2002 | Graybill |
| 6,524,104 B2 | 2/2003 | Matsutani et al. |
| 6,575,747 B1 | 6/2003 | Riitano et al. |
| 6,710,020 B2 | 3/2004 | Tenne et al. |
| 6,910,889 B1 | 6/2005 | Hickok |
| 7,014,743 B2 | 3/2006 | Zhou et al. |
| 7,776,310 B2 | 8/2010 | Kaplan |
| 2001/0034005 A1 | 10/2001 | Matsutani et al. |
| 2003/0144155 A1 | 7/2003 | Tenne et al. |
| 2004/0109823 A1 | 6/2004 | Kaplan |
| 2004/0173378 A1 | 9/2004 | Zhou et al. |
| 2006/0123336 A1 | 6/2006 | Altman et al. |
| 2007/0015107 A1 | 1/2007 | Mannschedel et al. |
| 2007/0284255 A1 | 12/2007 | Gorokhovsky et al. |
| 2008/0195196 A1 | 8/2008 | Asgari |

(Continued)

FOREIGN PATENT DOCUMENTS

| | | |
|---|---|---|
| CN | 2683059 | 7/2008 |
| EP | 0580019 | 1/1994 |

(Continued)

OTHER PUBLICATIONS

Rapoport et al; "High Lubricity of Re-Doped Fullerene-Like MoS2 Nanoparticles", Tribol Lett, 2012, 45, pp. 257-264.*
Ron et al (Nanoscale 6:5251-5259, 2014) (Year: 2014).*
Adini, AR, et al. "Alleviating fatigue and failure of NiTi endodontic files by a coating containing inorganic fullerene-like WS 2 nanoparticles." *Journal of Materials Research* 26.10 (2011): 1234-1242.
Adini AR, Redlich M, Tenne R. Medical applications of inorganic fullerene-like nanoparticles. Journal of materials chemistry. 2011;21(39):15121-31.
Alapati et al. "SEM observations of nickel-titanium rotary endodontic instruments that fractured during clinical use" Journal of Endodontics. Jan. 31, 2005;31(1):40-3.
Anderson et al. "Fracture resistance of electropolished rotary nickel-titanium endodontic instruments" Journal of Endodontics. Oct. 31, 2007;33(10):1212-6.

(Continued)

*Primary Examiner* — Craig D Ricci
(74) *Attorney, Agent, or Firm* — Mark S. Cohen; Pearl Cohen Zedek Latzer Baratz LLP

(57) ABSTRACT

A new approach is presented to reduce encrustation of catheters by the application of nanoparticles. It is demonstrated that the negatively surface charged nanoparticles produce coating films comprised of long-range domains in which the nanoparticles are self-assembled into a mosaic-like order, showing a relatively small tendency to agglomerate.

21 Claims, 7 Drawing Sheets

(56) References Cited

U.S. PATENT DOCUMENTS

| | | | |
|---|---|---|---|
| 2009/0032499 A1 | 2/2009 | Tenne et al. | |
| 2010/0105004 A1 | 4/2010 | Levy et al. | |
| 2013/0040261 A1 | 2/2013 | Kwon et al. | |
| 2015/0225237 A1 | 8/2015 | Tenne et al. | |

FOREIGN PATENT DOCUMENTS

| | | |
|---|---|---|
| GB | 2360790 | 10/2001 |
| JP | 6483252 | 3/1989 |
| JP | H01176097 | 7/1989 |
| JP | H06292690 | 10/1994 |
| JP | H1083252 | 3/1998 |
| JP | H11244307 | 9/1999 |
| JP | H 11287250 | 10/1999 |
| WO | WO 1996/027334 A1 | 9/1996 |
| WO | WO 1997/044278 | 11/1997 |
| WO | WO 2001/066676 | 9/2001 |
| WO | WO 2002/079686 A2 | 10/2002 |
| WO | WO 2006/123336 | 11/2006 |
| WO | WO 2007/008243 A2 | 1/2007 |
| WO | WO 2011/111044 A1 | 9/2011 |
| WO | WO 2014/033718 A1 | 3/2014 |
| WO | WO 2014/076693 A1 | 5/2014 |
| WO | WO 2014/130450 | 8/2014 |

OTHER PUBLICATIONS

Arango et al. "Coating and Surface Treatments on Orthodontic Metallic Materials" 2013, Coatings 3, 1-15.

Bojda et al. "Precipitation of Ni 4 Ti 3-variants in a polycrystalline Ni-rich NiTi shape memory alloy" Scripta materialia. Jul. 31, 2005;53(1):99-104.

Brinson et al. "Stress-induced transformation behavior of a polycrystalline NiTi shape memory alloy: micro and macromechanical investigations via in situ optical microscopy" Journal of the Mechanics and Physics of Solids. Jul. 31, 2004;52(7):1549-71.

Chen, Wei Xiang, et al. "Wear and friction of NiP electroless composite coating including inorganic fullerene WS2 nanoparticles." Advanced engineering materials 4.9 (2002): 686-690.

Cheung et al. "Defects in ProTaper S1 instruments after clinical use: fractographic examination" International Endodontic Journal. Nov. 1, 2005;38(11):802-9.

Condorelli et al. "Improvement of the fatigue resistance of NiTi endodontic files by surface and bulk modifications" International endodontic journal. Oct. 1, 2010;43(10):866-73.

Eggeler et al. "Wagner M. Structural and functional fatigue of NiTi shape memory alloys" Materials Science and Engineering: A. Jul. 25, 2004;378(1):24-33.

Friedman et al. "Fabrication of self-lubricating cobalt coatings on metal surfaces" Nanotechnology. Feb. 7, 2007;18(11):115703.

International Search Report for PCT Application No. PCT/IL2015/050021 dated May 10, 2015.

Katz, A., et al. "Self-lubricating coatings containing fullerene-like WS2 nanoparticles for orthodontic wires and other possible medical applications." *Tribology Letters* 21.2 (2006): 135-139.

Kim et al. "Cyclic fatigue and fracture characteristics of ground and twisted nickel-titanium rotary files" Journal of Endodontics. Jan. 31, 2010;36(1):147-52.

Kuhn et al. "Influence of structure on nickel-titanium endodontic instruments failure" Journal of Endodontics. Aug. 31, 2001;27(8):516-20.

Lange et al. "Update on ureteral stent technology. Therapeutic advances in urology" Aug. 1, 2009;1(3):143-8.

Liu et al. "Effect of deformation by stress-induced martensitic transformation on the transformation behaviour of NiTi" Intermetailics. Jan. 31, 2000;8(1):67-75.

Margulis et al. "Nested fullerene-like structures" Nature. 1993;365(6442):113-4.

Morgan "Medical shape memory alloy applications—the market and its products" Materials Science and Engineering: A. Jul. 25, 2004;378(1):16-23.

Nayan et al. "Effect of mechanical cycling on the stress-strain response of a martensitic Nitinol shape memory alloy" Materials Science and Engineering: A. Nov. 15, 2009;525(1):60-7.

Otsuka et al. "Physical metallurgy of Ti—Ni-based shape memory alloys" Progress in materials science. Jul. 31, 2005;50(5):511-678.

Parashos et al. "Rotary NiTi instrument fracture and its consequences" Journal of Endodontics. Nov. 30, 2006;32(11):1031-43.

Park et al. "Dynamic torsional resistance of nickel-titanium rotary instruments" Journal of endodontics. Jul. 31, 2010;36(7):1200-4.

Pelletier et al. "Structural and mechanical characterisation of boron and nitrogen implanted NiTi shape memory alloy" Surface and Coatings Technology. Sep. 30, 2002;158:309-17.

Peters OA. "Current challenges and concepts in the preparation of root canal systems: a review" Journal of endodontics. Aug. 31, 2004;30(8):559-67.

Peters et al. "Effect of liquid and paste-type lubricants on torque values during simulated rotary root canal instrumentation" International endodontic journal. Apr. 1, 2005;38(4):223-9.

Rao et al. "Synthesis of inorganic nanotubes" Advanced Materials. Nov. 13, 2009;21(42):4208-33.

Rapoport et al. "Hollow nanoparticles of WS 2 as potential solid-state lubricants" Nature. Jun. 19, 1997;387(6635):791-3.

Rapoport et al. "Applications of WS 2 (MoS 2) inorganic nanotubes and fullerene-like nanoparticles for solid lubrication and for structural nanocomposites" Journal of Materials Chemistry, 2005, 15(18), pp. 1782-1788.

Rapoport, L., et al. "Tribological properties of WS 2 nanoparticles under mixed lubrication." Wear 255.7 (2003): 785-793.

Redlich, Meir, et al. "In vitro study of frictional forces during sliding mechanics of "reduced-friction" brackets." American Journal of Orthodontics and Dentofacial Orthopedics 124.1 (2003): 69-73.

Sahoo et al. "Molecular Camouflage: Making Use of Protecting Groups to Control the Self-Assembly of Inorganic Janus Particles onto Metal-Chalcogenide Nanotubes by Pearson Hardness" Angewandte Chemie International Edition. Dec. 16, 2011;50(51):12271-5.

Sattapan et al. "Defects in rotary nickel-titanium files after clinical use" Journal of Endodontics. Mar. 31, 2000;26(3):161-5.

Spanaki et al. "Failure mechanism of ProTaper Ni—Ti rotary instruments during clinical use: fractographic analysis" International Endodontic Journal. Mar. 1, 2006;39(3):171-8.

Tenne et al. "Inorganic nanotubes and fullerene-like nanoparticles" Nat Nanotechnol. Nov. 2006;1(2):103-11.

Tenne, R., et al. "Polyhedral and cylindrical structures of tungsten disulphide." Nature 360.6403 (1992): 444-446.

Thompson SA. An overview of nickel-titanium alloys used in dentistry. International endodontic journal. Jul. 1, 2000;33(4):297-310.

Yared et al. "Influence of rotational speed, torque and operator's proficiency on ProFile failures" International Endodontic Journal. Jan. 1, 2001;34(1):47-53.

Zhang et al. "Influence of cross-sectional design and dimension on mechanical behavior of nickel-titanium instruments under torsion and bending: a numerical analysis" Journal of endodontics. Aug. 31, 2010;36(8):1394-8.

* cited by examiner

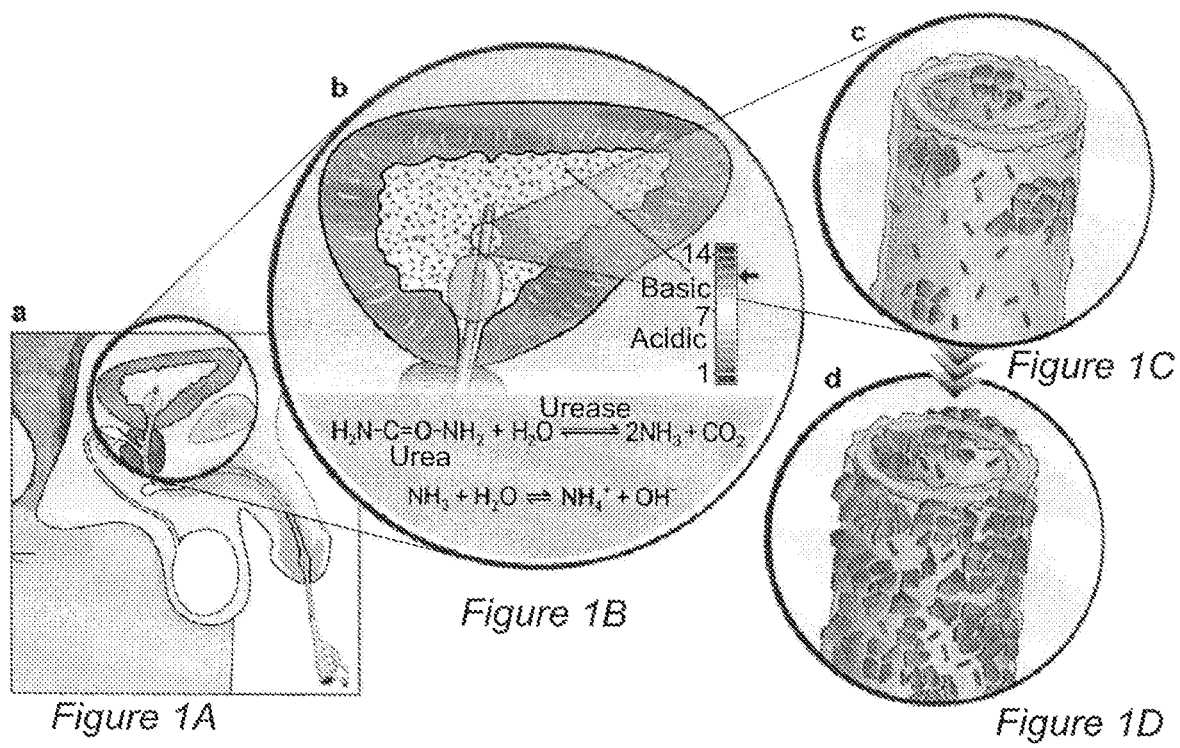
Figure 1A
Figure 1B
Figure 1C
Figure 1D
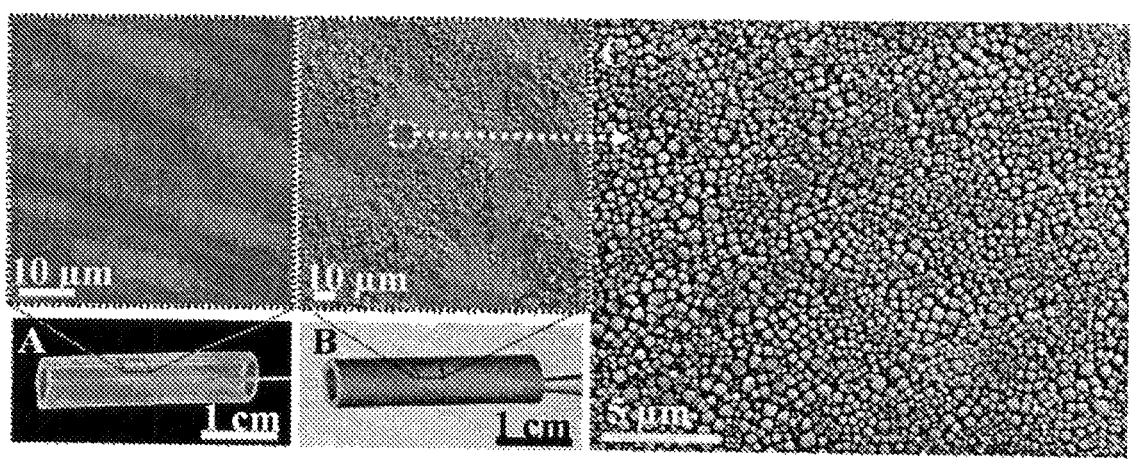
Figure 2A
Figure 2B
Figure 2C

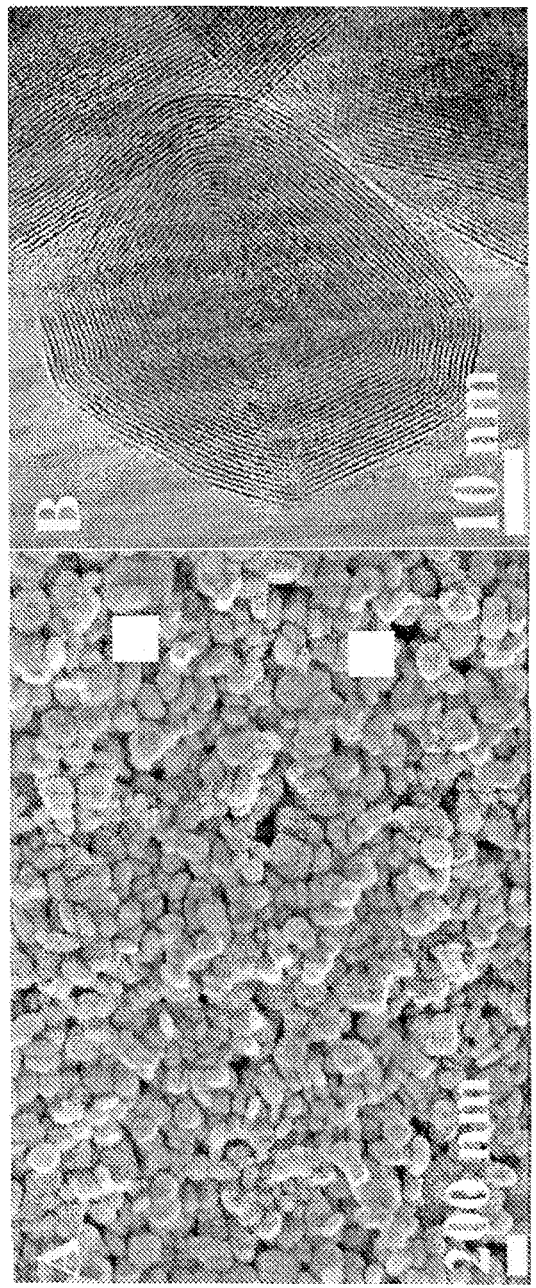
Figure 3A
Figure 3B
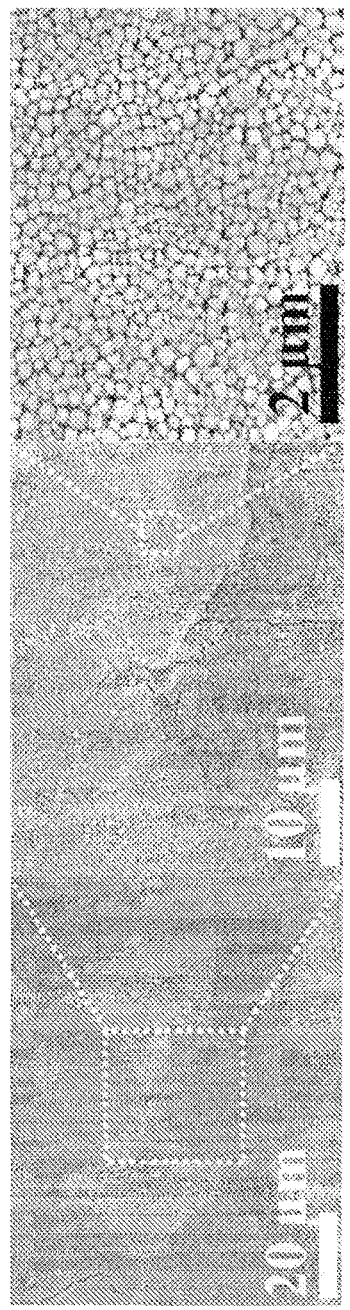
Figure 4

Figure 5A
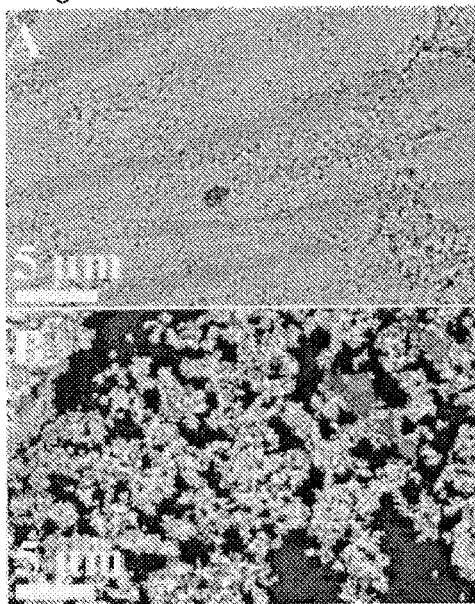
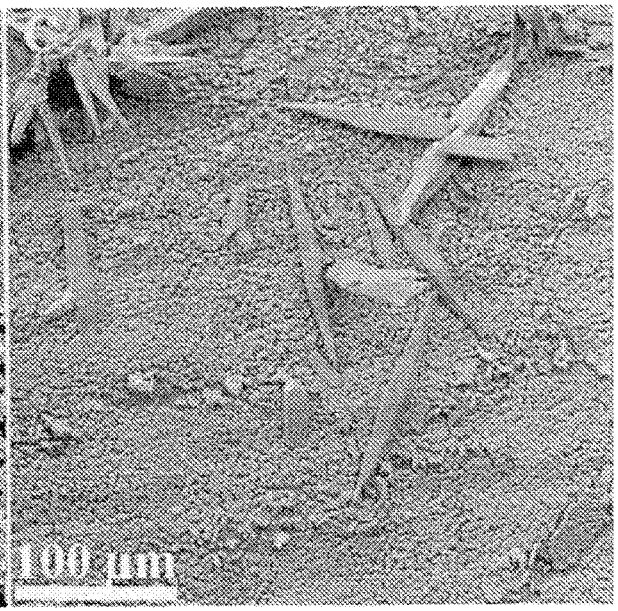
Figure 5B
Figure 5C
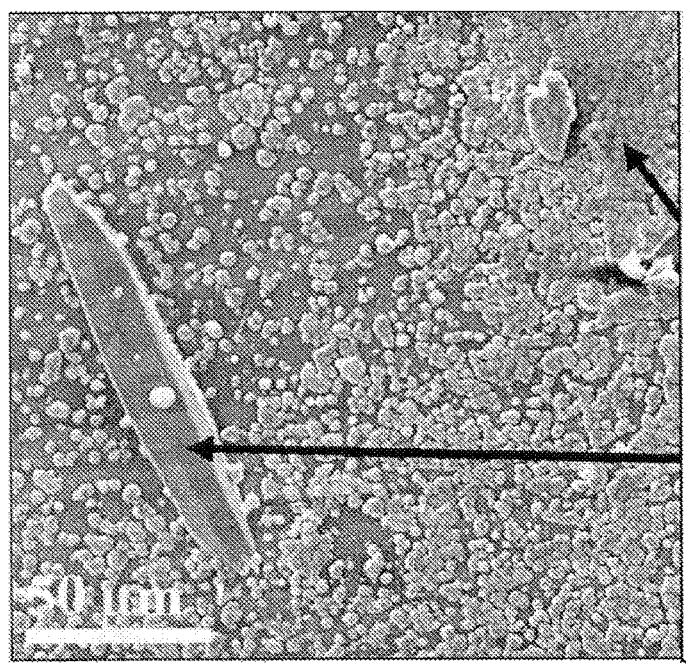
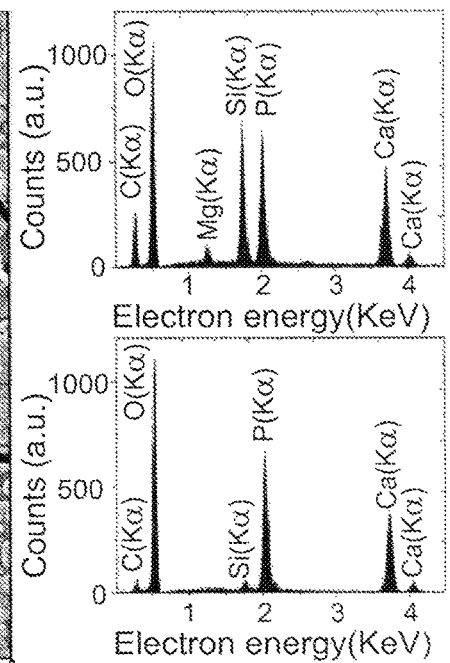
Figure 6

Figure 7A    Figure 7B
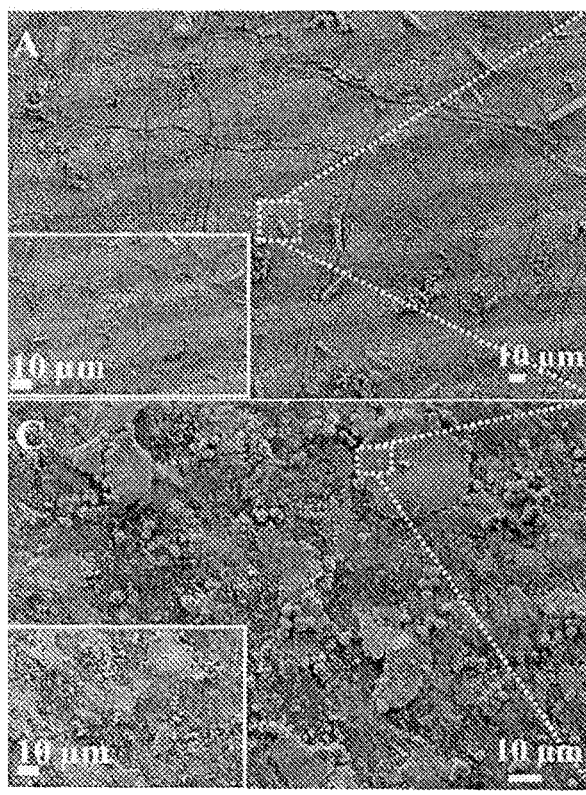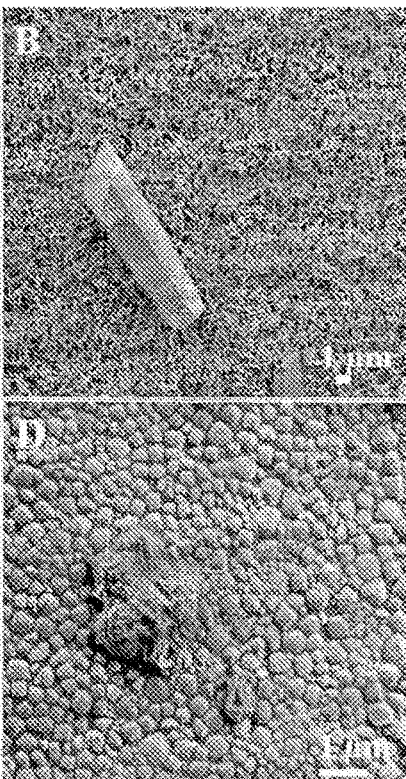
Figure 7C    Figure 7D
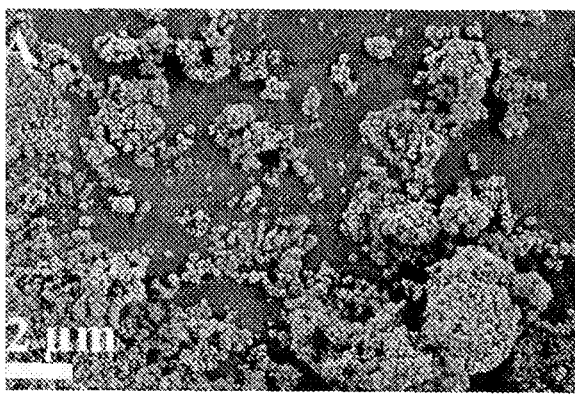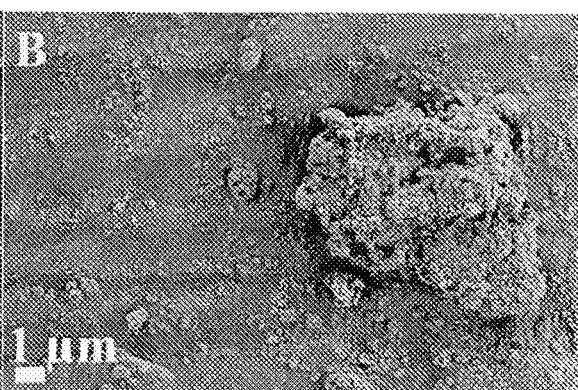
Figure 8A    Figure 8B

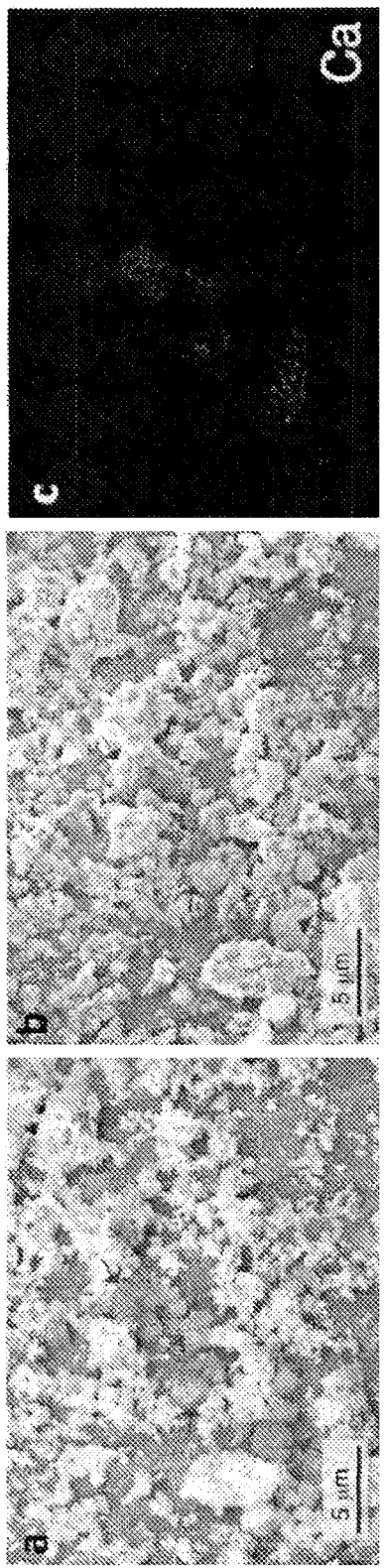
*Figure 9A*
*Figure 9B*
*Figure 9C*
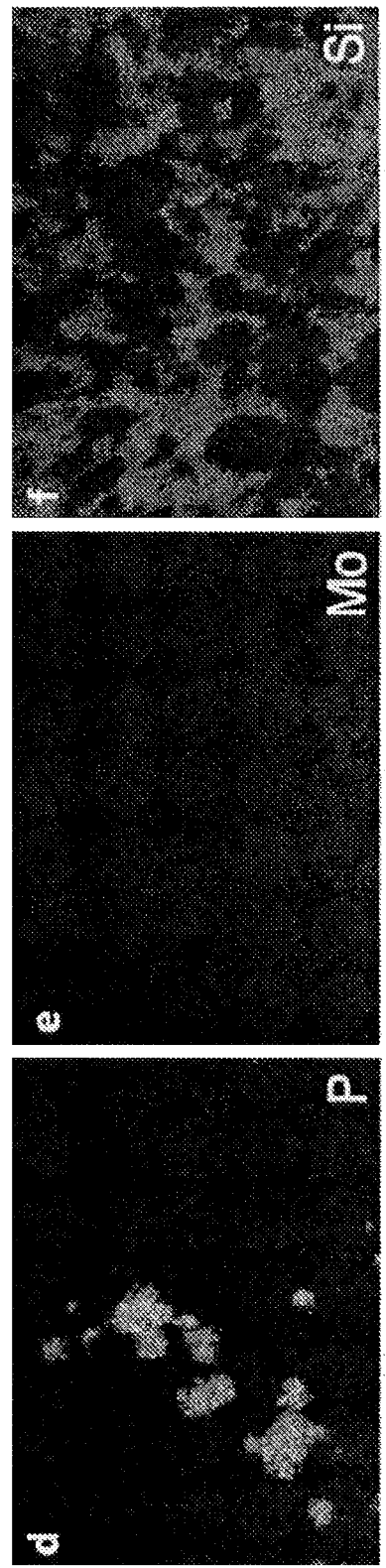
*Figure 9D*
*Figure 9E*
*Figure 9F*

ATTENUATION OF ENCRUSTATION OF MEDICAL DEVICES USING COATINGS OF INORGANIC FULLERENE-LIKE NANOPARTICLES

CROSS-REFERENCE TO RELATED APPLICATIONS

This application is a National Phase Application of PCT International Application No. PCT/IL2015/050021, International Filing Date Jan. 6, 2015, claiming priority and the benefit from U.S. Provisional application Ser. No. 61/923,841 filed on Jan. 6, 2014, which are hereby incorporated by reference.

TECHNOLOGICAL FIELD

The invention generally relates to a method of attenuating encrustation of medical devices using coatings of inorganic fullerene like nanoparticles.

BACKGROUND OF THE INVENTION

The complex processes of encrustation that occur in the urinary system are of a multifactorial nature interlacing chemical, biological and physical aspects. Infection-derived encrustation is a phenomenon mainly concerned with urethral catheters and its mechanism is considered to be well-established.

Consistent urine flow within the urinary tracts is central in maintaining the physiological balance of this system. Therefore, instrumentation of the urinary tracts with prosthetic medical devices (catheters, stents) is a common medical practice in various clinical situations. For selected patients long-term catheterization (LTC) periods are essential, translated into indwelling of an urological device in a patient's body for a period of over 30 days. Examples of these clinical scenarios include, most prevalently, disabled, elderly and terminally-ill patients. However, use of these medical devices in the long term jeopardizes patients' health. The primary problems in LTC comprise infection and encrustation, with a prevalence of 100 and 50%, respectively.

Encrustation-derived complications include obstruction, urine stasis and infection, mineral enucleation resulting in (bladder and kidney) stones, retrograde flow to upper urinary tract resulting in renal damage, and mechanical trauma to the urethra by the abrasive encrusted device. Furthermore, encrustation may even culminate with life-threatening episodes of either septicemia or shock.

REFERENCES

[1] R. Tenne, L. Margulis, M. Genut and G. Hodes, *Nature*, 1992, 360, 444-446.
[2] L. Margulis, G. Salitra, R. Tenne and M. Talianker, *Nature*, 1993, 365, 113-114.
[3] R. Tenne, *Nat. Nanotechnol.*, 2006, 1, 103-111.
[4] C. N. R. Rao and A. Govindaraj, *Adv. Mater.*, 2009, 21, 4208-4233.
[5] WO 2006/123336

SUMMARY OF THE INVENTION

Encrustation is resulted by crystallization out of ionic components in the urine on the biomaterial's surface either it is a catheter or stent or another medical device inserted to the body (e.g. dental implant). Infection-derived encrustation (unlike sterile encrustation) in the urinary system is a phenomenon mainly encountered in urethral catheters. The rate of encrustation incidence in the human-body once a catheter is indwelled is typically ~1 month. Consequently, catheter replacements are scheduled at maximum of 3 months intervals. The mechanism of infectious-encrustation is considered to be well-established. Its fundamental stages (FIG. 1) interlace chemical, biological and physical aspects, thus possessing a multifactorial nature. Concisely, initiation of the process is related to the access of bacteria into the normally-sterile urine. Where, the device serves as a substrate for a prospering bacterial colonization which constitutes a biofilm layer. Upon contact with device's surface, the bacteria form a gel-like matrix providing their surface-attachment and protection. Such that, the bacteria develop a resistance to antibiotic treatments due to the high durability the biofilm endows them. A biofilm bacterium (*Proteos Mirabilis*) synthesizes an enzyme (urease) which catalyzes the chemical reaction of urea hydrolysis, a component the urine is rich with. The released hydroxide ions (OH—) (FIG. 1) lead to an increase in the urinal pH, which normally is either neutral or slightly acidic (4.6-7.0).

Under elevated pH conditions, precipitation of the regularly-aqueous ionic salts of calcium and magnesium phosphate becomes feasible, since their solubility decrease beyond their supersaturation limit. These encrustation concretions attached and accumulated on the surfaces of the indwelled catheter. The main inorganic solid deposits found on in-vivo encrusted catheters are calcium and magnesium phosphates in the form of hydroxyapatite ($Ca_{10}(PO_4)_6(OH)_2$) and struvite ($NH_4MgPO_4.6H_2O$). Other calcium-phosphate phases, like brushite ($CaHPO_4.2H_2O$), were also detected on catheter encrustations.

Catheter biomaterials inevitably become encrusted to a certain degree with exposure to the urinary environment. The ordinary treatment for sick patients includes recurrent replacements of the blocked device, which sometimes require a surgically removal. This treatment does not put an end to this clinical problem; in fact, it merely opens a vicious circle. A great variety of efforts to counteract the problem of encrustation have been reported, using many different strategies and approaches. Nonetheless, so-far these investigations failed to eliminate it altogether.

The inventors of the invention disclosed in the present application have developed a methodology for reducing, diminishing or generally favorably modulating growth and attachment of encrustation materials from bodily tissues or fluids, e.g., urine, on surfaces of medical devices which are implantable or insertable into a body lumen for long periods of time, such as urological catheters. The methodology involves coating such devices with a film of fullerene-like nanoparticles (such as Re doped $MoS_2$ nanoparticles—Re:IF—$MoS_2$ NPs). The fullerene-like nanoparticles are attached directly to the device surface without needing a coating matrix or a coating composite substrate in which the nanoparticles are embedded. In other words, the methodology involves forming a coat, film or layer of the nanoparticles directly on the device surface.

Scanning electron microscopy (SEM), energy dispersive x-ray spectroscopy (EDS), x-ray photoelectron spectroscopy (XPS) and x-ray powder diffraction (XRD) analyses indicated a remarkable attenuation in encrustation occupation on the coated device, e.g., catheter, surfaces compared to neat devices, and as compared to devices where the nanoparticles have been embedded in a matrix material or a coating material formed on the surface.

The coated devices of the invention dramatically reduced existing difficulties associated with the use of such devices in current therapies. The coated devices of the invention are advantageous over their uncoated counterparts not only in their ability to provide stable functioning over time, reducing the need to have the devices explanted routinely, but also in reducing risks associated with sudden blockage due to encrustation build-up and biofilm formation, which routinely results in emergency hospitalization and increased risk for the patient.

The use of medical devices coated with nanoparticles embedded in a matrix material [e.g., WO 2006/123336] is also disadvantageous over devices of the invention, particularly where the matrix material embedding the nanoparticles is metallic in constitution. Such matrices do not provide stable functioning over time as the matrix material detaches itself and/or decomposes from the device surface causing increased risks due to toxicity and blockage by the debris.

Thus, the inventors of the present invention have embarked on developing medical devices which reduce, minimize or diminish the formation of encrustations on the surfaces of the medical devices placed in a subject's body for long periods of times, as defined herein, permitting safe and continued functioning of the device; and, as a consequence, reducing health risks and discomfort which are known to characterize presently available devices for the same application.

Thus, in one of its aspects, the present invention provides an implantable or insertable medical device, coated on at least one surface region thereof with a film of inorganic fullerene-like nanoparticles (IF nanoparticles), wherein the film of IF nanoparticles is formed directly on said at least one surface region, and wherein said at least one surface region of the device is intended for direct contact with at least one inner-body tissue of a subject's body.

In another aspect, the present invention provides an implantable or insertable medical device, coated on at least one surface region thereof with a material film, said material film consisting of inorganic fullerene-like nanoparticles (IF nanoparticles), and wherein said at least one surface region of the device is intended for direct contact with at least one inner-body tissue of a subject's body.

In yet another aspect of the invention, there is provided an implantable or insertable medical device, coated on at least one surface region thereof with a plurality of inorganic fullerene-like nanoparticles (IF nanoparticles), wherein the plurality of IF nanoparticles is formed directly on said at least one surface region, and wherein said at least one surface region of the device is intended for direct contact with at least one inner-body tissue of a subject's body.

In some embodiments, the film or coat of plurality of IF nanoparticles are adapted to prevent or inhibit deposition of encrustation and/or formation of a biofilm thereon after implantation in the subject.

In another aspect of the invention, there is provided an implantable or insertable medical device configured to be implanted or inserted in a subject, the device comprising an implantable unit or structure, wherein at least a surface region of said unit or structure being coated with a film of IF nanoparticles adapted to prevent or inhibit deposition of encrustation and/or formation of a biofilm thereon after implantation in the subject.

In a further aspect, there is provided a medical device comprising at least one unit or structure configured to be implanted or inserted in a subject, wherein at least a surface region of said unit or structure being coated with a film consisting of IF nanoparticles.

The medical device may be selected amongst devices which comprise at least one unit or structure which is implantable or insertable in a recipient and which are used for the purpose of diagnosis or in any medical procedure and which residence in the body of the patient may be long enough to result in the growth and attachment of adventitious materials or exudates, or to result in the formation of biofilms.

As used herein, the implantable or insertable medical device which at least one surface region thereof is intended for direct contact with an inner-body tissue may be any medical device which is used for the purpose of diagnosis or treatment in any of numerous pathological and non-pathological conditions in which a tissue, a gland, a tumor, a cyst, a muscle, a fascia, a skin region, an adipose, a mucous membrane, or any one organ or tissue becomes damaged or diseased, enlarged beyond its normal size, or stretched, obstructed, occluded, or collapsed of or from an adjacent body lumen or anatomical structure, or otherwise requires the use of such a device.

In some embodiments, the medical device is used in dentistry. Such devices may be selected amongst dental implants, orthodontic wires, orthodontic brackets, bands, and bonded or banded orthodontic attachments, which are susceptible to biofouling.

The medical device may be one typically utilized in the diagnosis or treatment of medical disorders associated with a body passageway such as blood vessels and other body lumens, wherein the passageway becomes or is susceptible to becoming blocked or weakened by, e.g., a tumor, restricted by plaque, weakened by an aneurysm, etc.

The medical device may also be one which is intended for bridging between two or more body organs, lumens or tissues.

The medical devices are further selected amongst such which are placed in a body region, tissue, organ or body lumen, or otherwise in contact with a body fluid which renders the device susceptible to encrustation. Thus, excluded are devices which are typically used in body regions or organs or tissues where encrustation is not characteristic.

In some embodiments, the medical device is a device which is implanted for periods of between days and months to years in a recipient.

In some embodiments, the medical device is one or more of endoprosthesis such as stents of any configuration, shape and size, including covered stents, stent-grafts biliary stents, urethral stents, ureteral stents, tracheal stents, coronary stents, pancreatic stents, gastrointestinal stents and esophageal stents; catheters; dialysis tubes; cannulas; sutures; or other medical device designed for placement (entirely or partially) in the body of a subject (human or non-human).

In some embodiments, the medical device is a hollow device for inserting through a body opening or through the skin (percutaneously) into a body cavity, duct, or vessel to permit or assist in fluid passage therethrough. In some embodiments, the device is suitable for positioning for long periods of times (days to months to years).

In some embodiments, the medical device according to the invention is a ureteral or urethral stent or catheter.

In some embodiments, the medical device is prosthesis. In other embodiments, the medical device is selected from vascular grafts and joints.

As stated above, the device need not be completely covered with a coat, film or a layer of the IF-nanoparticles in accordance with the invention. The IF coating should be implemented on a surface region of the medical device which is exposed to a physiological environment, and which as a result may be susceptible to encrustation.

Thus, the term "surface" according to the present invention relates to a surface region of the device, being of any size, shape and of any material, such as a metal (such as titanium), stainless steel, glass, plastic, silicones and others. One of the main causes of catheter failure, particularly in catheters which are clinically positioned in a body lumen to permit uninterrupted fluid passage, is blockage of the catheter lumen by encrustation or blood. Thus, the surface of the device may not only be the outer surface of the device, but also any inner surface of a tubular device.

The surface may be of a flexible or rigid material, which may be substantially two-dimensional or a three-dimensional curved surface. The surface may be of any smoothness. In some embodiments, the device is flexible.

The surface region covered by a coat, film or layer of IF nanoparticles may be the full surface of the device, or any portion thereof which is intended for inserting into the body of the patient. The coated surface region of the device may be an external or an inner surface thereof.

The IF coating or film formed on a surface region of the device, as detailed herein, comprises a plurality of inorganic fullerene-like (IF) nanoparticles, as known in the art. The coating may comprise any population of such nanoparticles, including those recited in patent applications or prepared according to processes recited in: PCT/IL2013/050933, PCT/IL2013/050732, WO 2011/111044, WO 2006/123336 and/or PCT/IL01/00204 each being incorporated herein by reference (re corresponding US applications/patents).

Without wishing to be bound by theory, the "inorganic nanoparticles" (for brevity used interchangeably hereinforth with the term "nanoparticles") are hollow, in some cases closed-cage nanoparticles of transition metal chalcogenides, metal dichalcogenides or metal halides, which may be single or multi-layered, having structures such as nanospheres, nanotubes, nested polyhedra, onion-like (multiwalled and singlewalled) and the like.

As a person skilled in the art would appreciate, the term "nanoparticle" should not be regarded as limiting the average size of the particles to the nanoscale. While in some embodiments the nanoparticles employed in accordance with the invention are fully in the nanoscale regime, in some other embodiments, particularly those relating to nanotubes, at least one of the particles' dimensions is in the nanoscale (e.g., width) while other dimensions (e.g., length) may be at the microscale.

In some embodiments, the nanoparticles are inorganic nanotubes (INT) or inorganic fullerene-like nanoparticles (IF).

In some embodiments, the nanoparticles are of the general formula $ML_n$, wherein M is a transition metal, L is a chalcogen and n is the number of chalcogen atoms L per each atom of the transition metal M. A transition metal includes all the metals in the periodic table from titanium to copper, from zirconium to silver and from hafnium to gold. In some embodiments, the transition metals are selected from Sn, In, Ga, Bi, Mo, W, V, Zr, Hf, Pt, Pd, Re, Nb, Ta, Ti, Cr and Ru.

The term "chalcogene" refers to atoms of the chemical elements belonging to group VIA (group 16) of the periodic table of the elements. In the context of the present invention, the term refers to an element selected from S, Se and Te. "Chalcogenide" thus refers to compounds which comprise a chalcogene ion, such as a sulfide, selenide and telluride.

Within the context of the present invention, although belonging to the group VIA elements, oxygen is not considered a chalcogene.

The chalcogen is selected from S, Se and Te.

In some embodiments, the inorganic nanoparticles are doped nanoparticles.

In some embodiments, the inorganic nanoparticles are of the general formula $A_{1-x}$-$B_x$-chalcognide, wherein A is either a metal or a transition metal or an alloy of such a metal/transition metal, B is a metal or a transition metal, and x being ≤0.3 and different from zero, provided that: A≠B.

In some embodiments, x is below 0.01, or below 0.005. In further embodiments, x is between 0.005 and 0.01.

The metal or transition metal or alloy of metals or transition metals is selected from the following atoms: Mo, W, Re, Ti, Zr, Hf, Nb, Ta, Pt, Ru, Rh, In, Ga, WMo and TiW.

B is a metal or transition metal selected from the following: Si, Nb, Ta, W, Mo, Sc, Y, La, Hf, Ir, Mn, Ru, Re, Os, V, Au, Rh, Pd, Cr, Co, Fe and Ni.

Within the nanostructure $A_{1-x}$-$B_x$-chalcognide, B and/or B-chalcogenide are typically incorporated within the $A_{1-x}$-chalcogenide. The chalcogenide is selected from S, Se and Te. For example, IF nanostructure to be used in the preparation of materials and composites of the invention may be IF—$Mo_{1-x}Nb_xS_2$, IF—$Mo(W)_{1-x}Re$—$S_2$, the alloys of $WMoS_2$, $WMoSe_2$, $TiWS_2$ and $TiWSe_2$, where Nb or Re are doped therein.

The term "incorporated" means that the B and/or B-chalcogenide are doped or alloyed uniformly within the $A_{1-x}$-chalcogenide lattice. The B and/or B-chalcogenide substitute the A atom within the lattice. Such substitution may be continuous or alternate substitutions. Continuous substitution are spreads of A and B within each layer alternating randomly (e.g., $(A)_n$-$(B)_n$, n>1). Depending on the concentration of incorporated B, it may replace a single A atom within $A_{1-x}$-chalcogenide matrix forming a structure of ( . . . A)$_n$-B-(A)$_n$-B . . . ). Alternate substitution means that A and B are alternately incorporated into the $A_{1-x}$-chalcogenide lattice ( . . . A-B-A-B . . . ). It should be noted that other modes of substitution of the B in the A-chalcogenide lattice are possible according to the invention. Since the A-chalcogenide has a layered structure, the substitution may be done randomly in the lattice or every 2, 3, 4, 5, 6, 7, 8, 9 or 10 layers.

In some embodiments, the chalcogen atom is replaced with a halide atom (such as Cl) and/or a pnicitide atom such as P and AS.

In some embodiments, a halide atom, e.g., Cl, substitutes a chalcogen atom, e.g., S.

In some embodiments, the metal chalcogenides and dichalcogenides are selected from $TiS_2$, $TiSe_2$, $TiTe_2$, $WS_2$, $WSe_2$, $WTe_2$, $MoS_2$, $MoSe_2$, $MoTe_2$, $SnS_2$, $SnSe_2$, $SnTe_2$, $RuS_2$, $RuSe_2$, $RuTe_2$, $GaS$, $GaSe$, $GaTe$, $InS$, $InSe$, $HfS_2$, $ZrS_2$, $VS_2$, $ReS_2$ and $NbS_2$. In some other embodiments, the metal chalcogenides and dichalcogenides are selected from $WS_2$ and $MoS_2$.

In some embodiments, the metal chalcogenide nanostructures of the formula $A_{1-x}B_x$-chalcogenide are selected from $W_{1-x}B_x$-chalcogenide, $Mo_{1-x}B_x$-chalcogenide, $Nb_{1-x}B_x$-chalcogenide and $Ta_{1-x}B_x$-chalcogenide.

In additional embodiments, the inorganic nanoparticles are selected from $WS_2$, $MoS_2$, $NiBr_2$, $NiCl_2$, $VS_2$, $TiS_2$ and $InS$.

In some embodiments, the nanoparticles are doped with dopant atoms. The term dopant atoms or doping atoms refers to atoms which are different from the atoms comprising the nanoparticles. In some embodiments, the dopant is present in the nanoparticle in a concentration lower than 1 at %. In other embodiments, the dopant is present in the nanoparticle in a concentration lower than 5 at %. The dopant atoms may be selected from atoms Si, Nb, Ta, W, Mo, Sc, Y, La, Hf, Ir, Mn, Ru, Re, Os, V, Au, Rh, Pd, Cr, Co, Fe, and Ni.

In some embodiments, doping is achieved by replacing the chalcogen atom with a halide atom (such as Cl) and/or a pnicitide atom such as P and AS. In some embodiments, a halide atom, e.g., Cl, substitutes a chalcogen atom, e.g., S.

In some embodiments, the nanoparticles are selected from Re doped nanoparticles and Nb doped nanoparticles.

In some embodiments, the nanoparticles are selected from Re:IF—$MoS_2$, Nb:IF-$MoS_2$, Re:IF-$WS_2$ and Nb:IF-$WS_2$.

In some embodiments, the nanoparticles are doped IF-$WS_2$, or doped IF-$MoS_2$.

In some embodiments, the IFs used in accordance with the invention are doped, or highly doped. In some embodiments, the dopant is present in the nanoparticle in a concentration lower than 1 at %. In other embodiments, the dopant is present in the nanoparticle in a concentration lower than 5 at %. In further embodiments, the dopant is present in the nanoparticle in a concentration lower than 0.1 at %. In other embodiments, the dopant is present in the nanoparticle in a concentration lower than 0.5 at %.

In some embodiments of the invention, the medical device is a ureteral or urethral stent or catheter, used to facilitate urinary drainage from the kidney to the bladder and from the bladder for the removal of the fluids from the body. The stent and/or catheter are typically utilized in patients having an obstruction or injury in the ureter or the urethra, or to protect the integrity of the organs during a medical manipulation.

In another aspect, there is provided a process for manufacturing an implantable or insertable medical device, the process comprising forming on at least a surface region of said device a film of IF-nanoparticles.

Generally, the region coated with the IF-nanoparticles may be formed by any method known in the art apart from embedding the nanoparticles in metal matrix films. In some embodiments, the IF-nanoparticles are embedded into the surface material of a ready-to-use device, as defined herein by thermal treatment of the device, by US energy, or by any other methodology known in the art. In other embodiments, the film is formed by forming bottom-up construction of a device, utilizing one or more material layers, the top most of which (i.e., the layer to be in direct contact with the bodily fluid or membrane) pre-embedding the IF-nanoparticles. In such a de-novo construction of a device, the IF-nanoparticles may be placed as a coat or a film on the top-most surface of the multilayered device, thereby providing the necessary protection against encrustation.

Thus, the ability to form such devices permits a process for reducing, diminishing or preventing the formation of encrustations on a surface region of an implantable or insertable medical device, the process comprising forming a coating or a film of IF nanoparticles as disclosed herein on said surface region prior to implanting or inserting said device into a body tissue, organ or body lumen.

The term "reducing, diminishing or preventing the formation of encrustation on a surface region of a device" refers to the ability of the coating present on said surface region to reduce, diminish or prevent the development of a sticky surface by bacteria, preventing the deposition of ammonia salts, calcium phosphates and other insoluble salts onto the surface of the device, and preventing blood clotting from being formed on the surface.

The coat or film or layer of IFs may be of any form and constitution. The term "layer of IFs" or any variation thereof, refers to a layer of IFs wherein the IFs coat a device surface region according to the invention and/or IFs embedded in the material making up the device region. The layer of IFs does not contemplate a layer of a foreign material (a material being different from the surface material and the IFs) acting as a matrix for holding or containing the IFs. In other words, the layer of IFs is not a layer of a composite material.

The IFs may be embedded in the device or unit material during the manufacturing process thereof or may be thereafter coated with a film consisting a population of said IFs.

The IF layer may be produced on a surface of a device, as further discussed below, by any means available. In some embodiments, the layer may be formed by sonication or by ultrasound. In other embodiments, the IF layer is formed by dipping, brushing, spraying or any other process known in the art.

Generally, the thickness of the IF layer is between 10 nm and 100 µm.

In some embodiments, the thickness of the IF layer is between 100 nm and 10 µm.

In some embodiments, the thickness of the IF layer is smaller than 1,000 µm. In some embodiments, the thickness of the IF layer is smaller than 100 µm. In some embodiments, the thickness of the IF layer is smaller than 10 µm. In some embodiments, the thickness of the IF layer is smaller than 10 µm. In some embodiments, the thickness of the IF layer is smaller than 1 µm.

In some embodiments, the thickness of the IF layer is smaller than 500 µm. In some embodiments, the thickness of the IF layer is smaller than 50 µm. In some embodiments, the thickness of the IF layer is smaller than 5 µm.

In some embodiments, the thickness of the IF layer is smaller than 1,000 nm. In some embodiments, the thickness of the IF layer is smaller than 100 nm. In some embodiments, the thickness of the IF layer is smaller than 10 nm. In some embodiments, the thickness of the IF layer is smaller than 1 nm.

In some embodiments, the thickness of the IF layer is smaller than 500 nm.

In some embodiments, the thickness of the IF layer is between about 100 nm and 500 nm.

In some embodiments, the IF layer is a monolayer of IF nanoparticles.

The invention further contemplates methods of inserting a medical device, as defined herein, into or through a body cavity and positioning the device in said body cavity for long periods of times (days to months to years), the method being adapted for minimizing or diminishing encrustation of the medical device while positioned for the indicated period of time in the cavity of the subject, the methods generally comprise inserting a device according to the invention, utilizing methods known in the art and suitably selected based on the specific parameters considered by a medical practitioner.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 1 is a schematic representation of infection-derived encrustation process occurring on long-term indwelled medical catheters and the chemical reactions develop in the urine during the process; FIG. 1A: The catheter is anchored in the bladder by an inflated balloon, from which, via a tube ends in the urethra, it leads the urine out of the body. The device serves as a substrate on which bacteria reside and thrive, constituting a stubborn and resistive biofilm. FIG. 1B: A potent biofilm's bacterium synthesizes the urease enzyme which catalyzes the chemical reaction of urea hydrolysis. Thus, hydroxide ions (OH—) are released to the urinal medium and elevate its pH. FIG. 1C: Precipitation of the calcium and magnesium phosphate salts (i.e. the encrustation stones) on the surfaces of the indwelled catheter is taking place under these new conditions. FIG. 1D: This process leads thereby to the blockage of the catheter and its dysfunction with elapsing of time.

FIG. 2 depicts catheters before and after coating with the Re:IF—$MoS_2$ nanoparticles; FIG. 2A—A photograph of a neat catheter specimen. The inset of FIG. 2A shows an SEM micrograph of the surface of an uncoated catheter. FIG. 2B—A photograph of a Re:IF—$MoS_2$-coated catheter specimen. The inset of FIG. 2B shows a low-magnification SEM micrograph of an Re:IF—$MoS_2$-coated catheter. FIG. 2C—A higher-magnification SEM micrograph of the Re:IF—$MoS_2$-coated catheter surface (mode 1) which is marked in the inset of FIG. 2B.

FIG. 3 is an electron microscopy imaging of rhenium-doped inorganic fullerene-like $MoS_2$ nanoparticles; FIG. 3A—SEM micrograph of Re:IF—$MoS_2$ powder. FIG. 3B—TEM micrograph of an individual Re:IF—$MoS_2$ nanoparticle.

FIG. 4 provides SEM micrographs of a Re:IF—$MoS_2$-coated catheter surface displaying a vast area on which the Re:IF—$MoS_2$ nanoparticles are self-assembled in a mosaic-like (mode 1) arrangement forming a closed-packed film. The Re:IF—$MoS_2$ nanoparticles film is also continuous over this enlarged surface area.

FIG. 5 provides SEM (BSE mode) micrographs of encrusted, Re:IF—$MoS_2$-coated and uncoated, catheters (both were jointly incubated in the same bath). FIG. 5A—Surface of a Re:IF—$MoS_2$-coated catheter. Encrustation concretions are minor. The imaged domain of the Re:IF—$MoS_2$ nanoparticles coating displays the closed-pack mosaic-like arrangement of the Re:IF—$MoS_2$ nanoparticles (mode 1). FIG. 5B—Another imaged coating domain (BSE mode of the SEM) on the same Re:IF—$MoS_2$-coated catheter surface as in FIG. 5A—Encrustation concretions (red arrows) are clearly distinguished by their darker appearance in comparison to the Re:IF—$MoS_2$ nanoparticles. The coating domain here contains rather clumped nanoparticles (mode 2). FIG. 5C—Surface of an uncoated catheter. Encrustation precipitates cover most of the surface by both the elongated and globular encrustive stones.

FIG. 6 provides EDS spectra of the two in-vitro encrustation morphologies. The arrows are directed to the adequate deposit's morphology on the SEM micrograph, from which the spectra were generated.

FIG. 7 provides SEM micrographs of encrusted, both uncoated and Re:IF—$MoS_2$ nanoparticles-coated, catheters after a joint in-vitro encrustation process. The solid precipitants of encrustation are highlighted by a pink coloration to allow easy distinction between them to the Re:IF—$MoS_2$ nanoparticles. FIG. 7A—The surface of a neat catheter specimen after its incubation in the encrustation model. Encrustation covers most of the surface forming a crust ("carpet"), on which elongated needle-like crystals are scattered. The original SEM micrograph is shown in the downright inset. The texture of the crust can be noticed by the high-magnification SEM micrograph in FIG. 7B. FIG. 7C—The surface of an encrusted catheter which was pre-coated by Re:IF—$MoS_2$ nanoparticles. The original SEM micrograph is shown in the downright inset. The sporadically-growth of encrustation stones is displayed. A high-magnification SEM micrograph of the encrusted Re:IF—$MoS_2$-coated catheter is shown in FIG. 7D.

FIG. 8 provides SEM micrographs of Re-doped and undoped IF-$MoS_2$ nanoparticles. FIG. 8A—A clumped (mode 2) packing of the Re:IF—$MoS_2$ coating on the surface of a silicone catheter. FIG. 8B—Typical undoped IF-$MoS_2$ coating on the silicone catheter.

FIG. 9 provides SEM (BSE and SE modes) imaging of the encrusted surface of a Re:IF-MoS2-coated catheter and elemental mapping by EDS of the coincident surface. FIG. 9A—SEM (BSE mode) and FIG. 9B—SEM (SE mode) micrographs of the EDS-mapped area, with the stones delineated by red arrows. The BSE allows clear discrimination between the Re:IF—$MoS_2$-nanoparticles coating and encrustation stones (see arrows) in FIG. 9A. In contrast, as seen in FIG. 9B, the contrast is insufficient to distinguish between the IF NP and the stones by the SE detector. This discrimination becomes prominent once small stones are to be identified. The EDS maps of FIG. 9C calcium and FIG. 9D phosphorus coincide with darker-gray imaged species (encrustation stones) in FIG. 9A while the map of FIG. 9E which highlights the molybdenum surface-distribution, is equivalent with the brighter-grey species (Re:IF—$MoS_2$ nanoparticles). FIG. 9F—The silicone distribution map is also coincident with the darkest substrate-domains in FIG. 9A. This confirmation between the EDS maps and the SEM-BSE mode micrographs allows relying on the fast BSE mode for the quantitative analysis over an enlarged (32,000 $\mu m^2$) area, which cannot be performed by the slow and tedious EDS analysis.

FIG. 10 provides XPS and XRD spectra of an uncoated and Re:IF-MoS2-coated catheter specimens after a joint incubation in the encrustation model.

DETAILED DESCRIPTION OF EMBODIMENTS

Figure 10A:
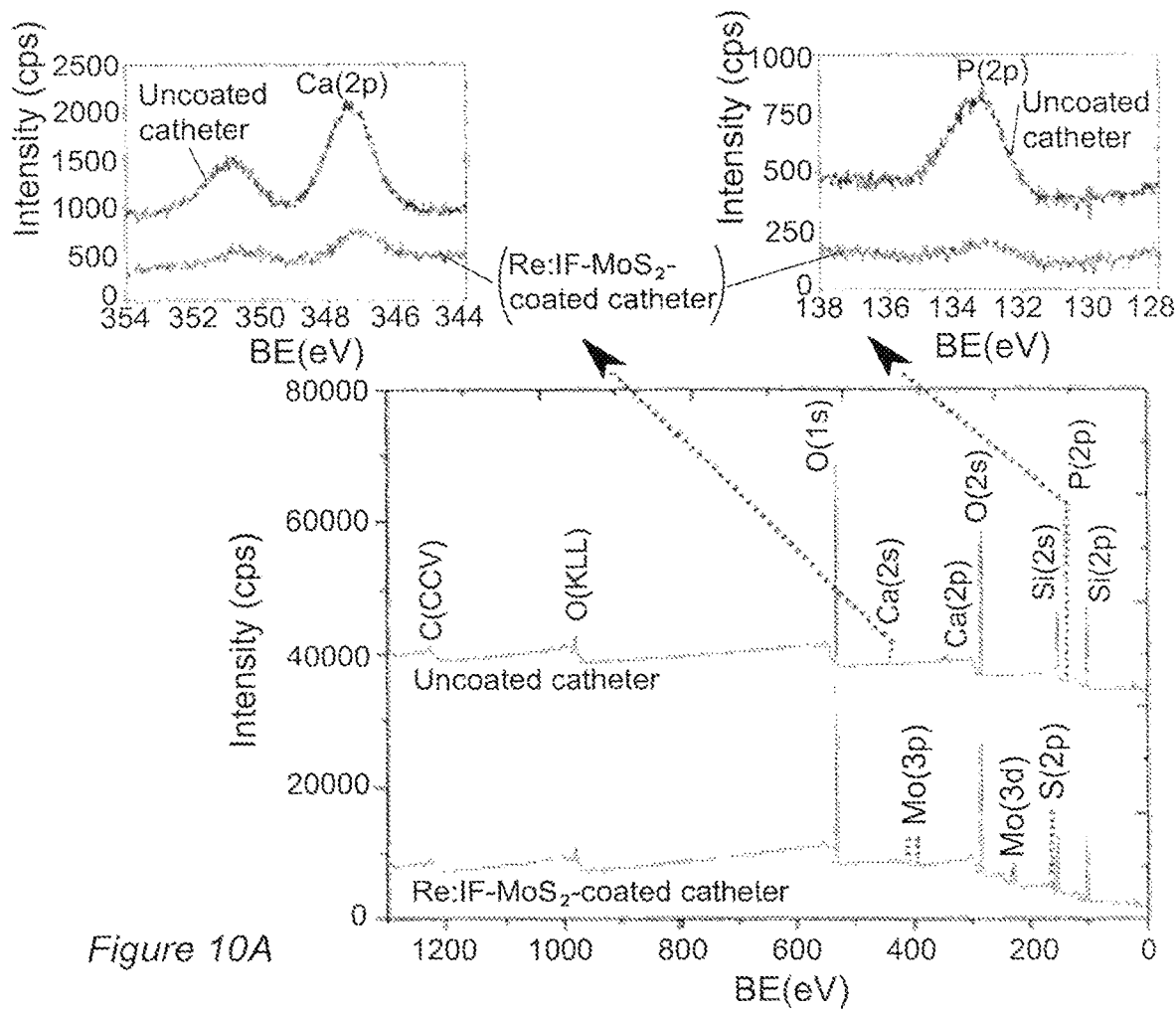
FIG. 10A—XPS broad-scans and highly-resolved binding energies peaks of calcium (2p) and phosphorus (2p) in the upper insets.

In the study leading to the invention disclosed herein, a commercial all-silicone catheter was coated with Re:IF—$MoS_2$ nanoparticles after a deagglomeration process. A joint incubation of uncoated and Re:IF—$MoS_2$-coated catheter specimens in an in-vitro model of a catheterized urinary tract under encrustation conditions was followed. Encrustation deposits which were developed on the uncoated and Re:IF—MoS$_2$-coated catheter surfaces were comparatively assessed.

There exists no single standard for an in-vitro model simulating encrustation. The use of artificially made urine provides a very convenient way for comparative studies, where a large series of experiments have to be carried out in order to evaluate the efficacy of a given technology.

Nanoparticles of inorganic layered compounds, such as WS$_2$ and MoS$_2$, are known to form a fullerene-like structure. These nanoparticles were first reported in 1992 [1,2] and were discussed extensively in several review papers [3,4]. A SEM micrograph of Re:IF—MoS$_2$ powder is shown in FIG. 3A. The structure and shape of an individual IF-MoS$_2$ nanoparticle is shown by the transmission electron microscopy (TEM) micrograph in FIG. 3B. Each polyhedral multilayer nanoparticle is made of closed MoS$_2$ layers and sizing ~5-200 nm Since an IF-MoS$_2$ nanoparticle is a seamless closed-cage moiety, no structured-edges comprising plenty of dangling bonds are attendant. Hence, each nanoparticle is enveloped by van der Waals surfaces of fully-saturated bonded (sulfur-terminated) atoms, possessing a low surface energy of 20 meV/Å2. Therefore, the nanoparticles exhibit very low affinity to their environment and they can easily roll or slide. Their unique atomically smooth topology (other than a few defects) and the fully saturated-bonds on their surfaces confer these nanoparticles (IF-WS$_2$, IF-MoS$_2$) superior solid-lubrication behavior, which has been exploited commercially.

Herein, the presence of a thin film of IF nanoparticles, such as the Re:IF—MoS$_2$ nanoparticles on the surfaces of a prosthetic device is shown to lead to a substantial attenuation in the encrustation on the catheter surface. Without wishing to be bound by theory, it is believed that their atomically smooth, passivated-surface and negative surface charge of the nanoparticles delegate the device surface with low drag and adhesive characteristics, thereby minimizing the encrustation phenomena on urological devices. Indeed, Re:IF—MoS$_2$ film coating was found to increase the indwelling durability and decreasing associated morbidities to the patient.

Results and Discussion

Re:IF—MoS$_2$ Nanoparticles Coating

FIG. 2 shows photographs and SEM micrographs of uncoated (bare) and Re:IF—MoS$_2$-coated catheter specimens. Native catheters had a transparent appearance (FIG. 2A) and their surfaces were found to be generally smooth with fine surface-dimples (inset of FIG. 2A). FIG. 2B demonstrates the successful application of the Re:IF—MoS$_2$ nanoparticles on the catheter specimens by the production of a uniform gray coating layer. Although, detailed SEM inspections of the Re:IF—MoS$_2$-coated catheters revealed that the coatings were not totally continuous on the entire catheter surface, i.e., small bald areas were observed within the coating films (inset of FIG. 2B). Furthermore, the Re:IF—MoS$_2$ coating was characterized by bimodal domains. Most often, Re:IF—MoS$_2$-coated domains displayed self-assembly of the nanoparticles into closed-packed arrays with a mosaic-like appearance (mode 1) (FIG. 2C, and also FIGS. 4 and 5A). It was noticed however, that the mosaic-like pavement by nanoparticles of the catheters surfaces was found to be much continues and extended as increased periods of staying in the well-deagglomerated coating's solution were held (FIG. 4).

Additionally, certain Re:IF—MoS$_2$-coated domains displayed a somewhat clumped arrangement (mode 2) of the nanoparticles (inset of FIG. 2B, and FIGS. 5B, 6A). Remarkably, undoped IF-MoS$_2$ nanoparticles were appreciably more agglomerated and clumped (FIG. 6), and consequently were not as effective in preventing encrustation as the doped nanoparticles coatings. Moreover, the Re:IF—MoS$_2$-coating of the catheter surfaces exhibited a long-term robustness. It might be related to a mechanically interlocking of the nanoparticles on the catheters surfaces as a result of a fine swelling.

Encrustation Assessment

Encrustation was gradually developed with time in the simulated urinary environment. After incubation periods of several hours, the initially-clear urine solution was converted into a highly-hazed appearance. This conversion indicated supersaturation of colloidal stones in the urinal medium, i.e., incidence of urea hydrolysis, ammonia release and its decomposition to OH-alkalizing ions (FIG. 1). A compact accumulation of precipitates on the vessel's bottom and walls followed. The experiments were stopped at this point and the catheters were removed out of the solution. During the incubation period the pH of the urine solution increased from 6.4-6.5 to 7.5-7.6. Typically, the turbidity appears when the pH of the solution exceeds the value of ~7. Clearly, the lower the concentration of the enzyme, the longer it takes for the solution to become hazed. The urease enzyme which was utilized during the sets of experiments was found to potently catalyze the urea decomposition. A minor amount of enzyme (5 ppm) was added to the system in the beginning of each (encrustation) experiment in order to decelerate the process to a period of a few hours. This time period was nevertheless much faster than in-vivo encrustation. However, the current simulation employed severe conditions than the (slower) clinical situation.

FIG. 7 shows SEM micrographs of both uncoated (FIG. 7A-B) and Re:IF—MoS$_2$-coated (FIG. 7C-D) catheter surfaces after an in-vitro encrustation process (see also FIG. 5). The SEM micrographs are colored to facilitate a rapid discrimination between encrustation precipitates and the coating's nanoparticles. The insets of FIGS. 7A and 7C display the original (without coloration) SEM micrographs for comparison. The SEM examinations showed that, on both surface types, the solid precipitates were composed of two major morphologies: spherical precipitate with a perforated and poorly crystalline structure and elongated needle-like crystals.

Indeed, chemical analysis of the encrusted surfaces by EDS analyses confirmed the growth of calcium- and phosphorus-containing stones. FIG. 8 exhibits the EDS spectra (accompanied by the respective SEM micrograph) which were generated from the two major typical morphologies of the grown deposits.

TABLE 1

EDS elemental composition of the two distinct morphologies of the in-vitro encrustation deposits.
Structural EDS results [at %]

| Morphology | C (K) | O (K) | Si (K) | P (K) | Ca (K) | Mg (K) | Ca/P |
|---|---|---|---|---|---|---|---|
| Brushite | 11.8 | 65.2 | 0.7 | 11.9 | 10.4 | — | 0.9 |
| Hydroxyapatite | 32.3 | 46.8 | 5.5 | 7.1 | 7.2 | 1.0 | 1.0 |

Table 1 quantitatively summarizes the EDS results. A small magnesium quantity was observed in the spectra of the globularly-shaped deposits. Nevertheless, struvite (MgNH$_4$PO$_4$.6H$_2$O) crystals were not observed in these series of experiments, most likely due to the low-basic urine pH in the current experimentation, which in most cases did not exceed 7.5. The experimentally observed Mg atoms are believed to be incorporated in the poorly crystalline apatite precipitate. The Ca/P ratio in both the elongated crystals and the structure-less stones was close to 1. This ratio is the typical for brushite whereas it deviates markedly from the composition of (fully-crystallized) hydroxyapatite (1.6). As it is further detailed below, comparatively XRD and XPS analyses of the surfaces of uncoated and Re:IF—MoS$_2$-coated catheter specimens also confirmed presentation of calcium-phosphate stones.

The Re:IF—MoS$_2$ Nanoparticles Effect on Encrustation and its Quantification

Different growth and attachment modes of the encrustive solids were found on uncoated catheter samples (FIG. 7A-B) in comparison to those on Re:IF—MoS$_2$-coated ones (FIG. 7C-D). These two specimens were incubated jointly in the same run, and this experiment was repeated a great number of times, revealing this difference reproducibly. Plain catheters were found to possess a continuous poorly crystalline crust ('carpet') over the entire surface, consisting of fused globular stones (see also FIG. 5B and FIG. 8). On which, the elongated and faceted crystals were scattered singly or as "flowers" with a common root in the center. Contrarily (FIG. 7C-D), only few and sporadically distributed stones occurred on the Re:IF—MoS$_2$-coated catheters (see also FIG. 5A-B). As was already mention, FIG. 7 displays the identical but colored SEM micrographs to enhance the discernment between encrustation stones and the Re:IF—MoS$_2$ nanoparticles. A clear discrimination between the encrusted stones and the Re:IF—MoS$_2$ nanoparticles usually requires application of higher SEM magnifications (FIG. 7D). Actually, the micrograph in FIG. 7C is not the most typical micrograph; the micrograph was chosen to be displayed since the encrustation growth's phenomenon on Re:IF—MoS$_2$-coated catheters is hardly observable under low-magnification in the secondary electron (SE) mode. More commonly, however, encrustation deposits on most of the scanned areas in the analyzed Re:IF—MoS$_2$-coated catheters were much smaller and distant from one another. In fact, the nucleation density of encrustation was appreciably smaller on the Re:IF—MoS$_2$-coated catheters compared to the encrusted uncoated catheter specimens. Importantly, although the Re:IF—MoS$_2$ coating was not fully-continuous or uniform, the degree of encrustation was greatly diminished on the entire catheter surface, i.e., even Re:IF—MoS$_2$-uncoated areas on the catheter substrate were rarely encrusted. This fact may indicate that small patches of the encrustation film can be easily uprooted and washed away as a Re:IF—MoS$_2$-coating is on the catheter surfaces.

Time-dependent experiments showed that the amount of encrustation deposits increased with elongated incubation times for either the uncoated or Re:IF—MoS$_2$-coated catheters. Longer incubation periods led to creation of a thicker compact calcium phosphate films on the uncoated catheters. On the other hand, in the case of the Re:IF—MoS$_2$-coated samples, new nuclei were not observed to be formed to a noticeable amount, but an enlargement of the already existing, sporadically distributed, calcium-phosphate precipitates was observed with longer incubation time, mainly in the vertical direction.

Using backscattering electron imaging mode (BSE) an enlarged surface area (32,000 μm$^2$) over the encrusted Re:IF—MoS$_2$-coated catheter specimen could be carefully analyzed (see Materials and methods). The BSE mode was utilized since the deposited nanoparticles and encrusted stones were barely distinguishable using the SE detector at lower magnifications (which could allow the examination of larger surface areas on each sample) (compare FIGS. 9A and 9B). As seen in FIG. 9B, an evenly-gray appearing represents the crust in the BSE-generated micrograph, which is much darker from the brighter gray-level of the nanoparticles. FIG. 9C-F exhibits verification of the fidelity of the much faster BSE analyses by a preceded EDS-elemental mapping of the same area. Each (rather long scan-time) EDS-map highlights the surface distribution of a single element of this sample. The congruence between the locations of stones as reflected from the Ca- and P-EDS maps and the BSE signal is clear. Thus, the BSE analysis revealed that the portion of encrusted area over the enlarged surface (32,000 μm$^2$) on the Re:IF—MoS$_2$-coated catheter was 0.44% compared to 92.9% over a similar area of the uncoated catheter.

TABLE 2

Quantification by EDS of encrustation stones on pristine and encrusted (uncoated and Re:IF-MoS$_2$-coated) catheters.

| | EDS Encrustation quantification [at %] | | | | | | | |
|---|---|---|---|---|---|---|---|---|
| Specimen | C(K) | O(K) | Si(K) | Mo(L) | S(K) | P(K) | Ca(K) | Mg(K) |
| Pristine catheter | 35.9 | 31.7 | 32.4 | 0.0 | 0.0 | 0.0 | 0.0 | 0.0 |
| Encrusted uncoated catheter | 26.9 | 37.3 | 16.5 | 0.0 | 0.0 | 8.6 | 10.1 | 0.6 |
| Encrusted IF-coated catheter | 28.9 | 20.5 | 19.2 | 10.7 | 17.0 | 1.9 | 1.2 | 0.6 |

Table 2 presents an elemental-quantification by EDS of uncoated and Re:IF—MoS$_2$-coated catheter surfaces after an encrustation process. The EDS analysis also found a considerable diminution of encrustation on the encrusted Re:IF—MoS$_2$-coated specimen. Specifically, the Ca and P content were 10.1 and 8.6 at % (respectively) for the neat specimen against 1.2 and 1.9 at % for the Re:IF—MoS$_2$-coated one. This result is consistent with the SE and BSE analyses.

A couple of catheter specimens were additionally studied by XPS. FIG. 10A presents the broad-scans of encrusted, Re:IF—MoS$_2$-coated and uncoated, catheters, together with the highly-resolved binding energies peaks of Ca(2p) and P(2p). Detailed atomic percent composition of the catheter surfaces achieved by the XPS measurements is presented in Table 3. The pronounced difference in the contents of encrustation-related elements is clearly displayed by the XPS results: the atomic concentrations of Ca(2p) and P(2p) for the uncoated catheter were 0.74 and 0.99 at %, respectively. The concentration of these atoms was reduced to 0.21 and 0.15 at % for the Re:IF—MoS$_2$-coated catheter. The atomic percent ratio of Mo to S on the Re:IF—MoS$_2$-coated specimen was 0.5.

TABLE 3

XPS elemental composition of encrusted and non-encrusted,
both uncoated and Re:IF—MoS$_2$-coated, catheter specimens.

XPS results [at %]

| | Catheter Surface | Ca(2p) | P(2p) | Si(2p) | O(1s) | C(1s) | S(2s) | S(2p) | Mo(3d) |
|---|---|---|---|---|---|---|---|---|---|
| Non-encrusted specimens | uncoated | — | — | 24.46 | 23.69 | 51.48 | — | — | — |
| | Re:IF—MoS$_2$-coated | — | — | 20.30 | 20.47 | 43.28 | 6.21 | 6.49 | 3.13 |
| Encrusted specimens | uncoated | 0.74 | 0.99 | 22.75 | 24.26 | 51.25 | — | — | — |
| | Re:IF—MoS$_2$-coated | 0.21 | 0.15 | 22.17 | 23.07 | 48.83 | 2.13 | 2.31 | 1.15 |

Figure 10B:
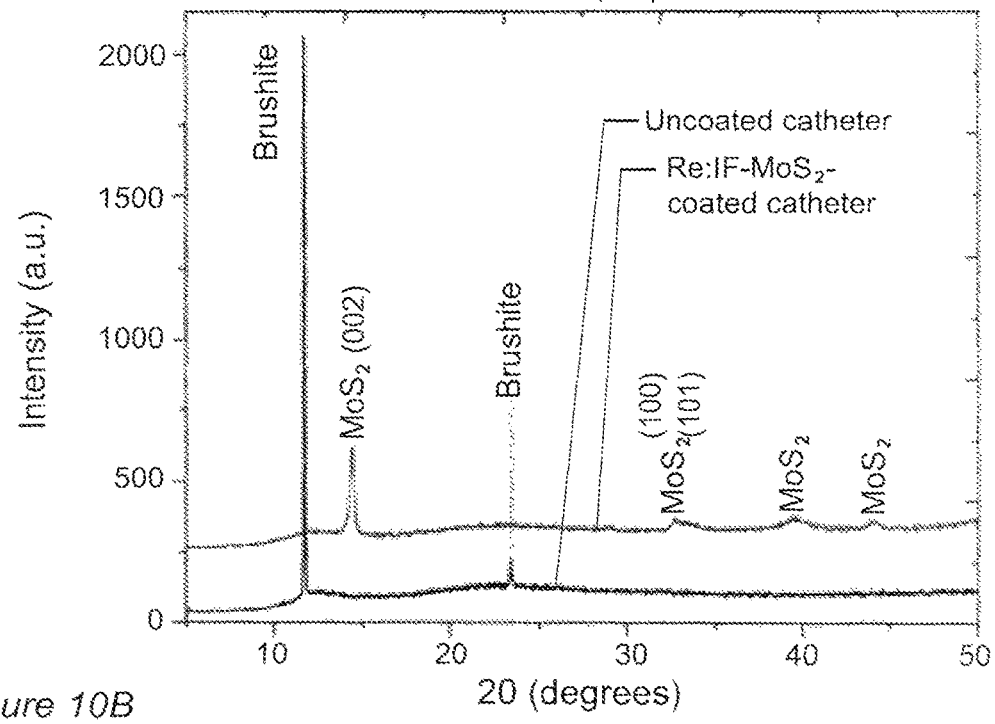
FIG. 10B—XRD spectra of the encrusted catheter specimens confirmed the presence of calcium-phosphate deposits on the uncoated surfaces while for the Re:IF—$MoS_2$-coated surface, the encrustation signals were smaller than the detection limit (0.5 wt %) of the instrument.

XRD measurements (FIG. 10B) of the encrusted uncoated specimen identified two intense peaks in 2θ values of 11.6 and 23.4 degrees, which can be assigned to the calcium-phosphate phase of brushite (black spectrum in FIG. 10B). The poorly crystalline hydroxyapatite could not be identified in this pattern. The XRD pattern of the encrusted Re:IF—MoS$_2$-coated catheter exhibited the MoS$_2$ peaks, while the brushite phase has largely vanished, confirming thereby the level of encrustation on this substrate which was under the detectable amount (0.5 wt %).

The experimental results principally demonstrate that the self-assembled Re:IF—MoS$_2$ nanoparticles film has a clear attenuating effect on the encrustation of all-silicon catheters.

Stones of similar types were detected on both the uncoated and Re:IF—MoS$_2$-coated catheter samples. Therefore, the presence of the Re:IF—MoS$_2$ nanoparticles on the coated catheter specimens influenced neither the morphology nor the chemical composition of the in-vitro encrustation. However, the difference in the degree of encrustation was consistently detected regardless of the technique used for the analysis.

The exact mechanism of the encrustation suppression on Re:IF—MoS$_2$-coated catheters is not fully comprehensible, yet. Nevertheless, a few key physio-chemical properties of these nanoparticles might provide guidelines for this mechanism. Particularly, their charge, low surface free energy and nano-texture-unique properties which are delegated to the coated catheter surface. Therefore, the presence of the nanoparticles film on the catheter surface alters its nano-structure, as well as its chemistry, influencing thereby the physio-chemical characteristics of the catheter surface.

Two different encrustation mechanisms can be considered, one involves a direct nucleation of the hydroxyapatite and brushite at stable surface-sites enabling its further growth on the available area. Simultaneously, stones nucleate and grow in the solution and subsequently these colloidal nanoparticles precipitate/adhere on the catheter surface.

The observed massive supersaturation in the urine during encrustation experiments indicates the enormous amount of colloidal stones surrounding each incubated catheter specimen. This situation introduces an abundant possibility for stones precipitation and adherence. However, as investigation of the surface-structure of the Re:IF-coated catheters showed, the colloidal stone particles approaching a catheter specimen from the bulk solution encounter a totally different architecture than the smooth substrate of a neat catheter specimen. Generation of the special surface-nanostructure by self-assembly of the negatively-charged Re:IF—MoS$_2$ nanoparticles into two-dimensional close-packed arrays (FIG. 2C, 4, 6A) produced a compact dense array of nano-distant bumps. This nanoparticles arrangement, might reduce the availability of contact-points for anchoring stones to the Re:IF—MoS$_2$-coated catheter surface, which is an established mechanism for self-cleaning surfaces.

Figure 11:
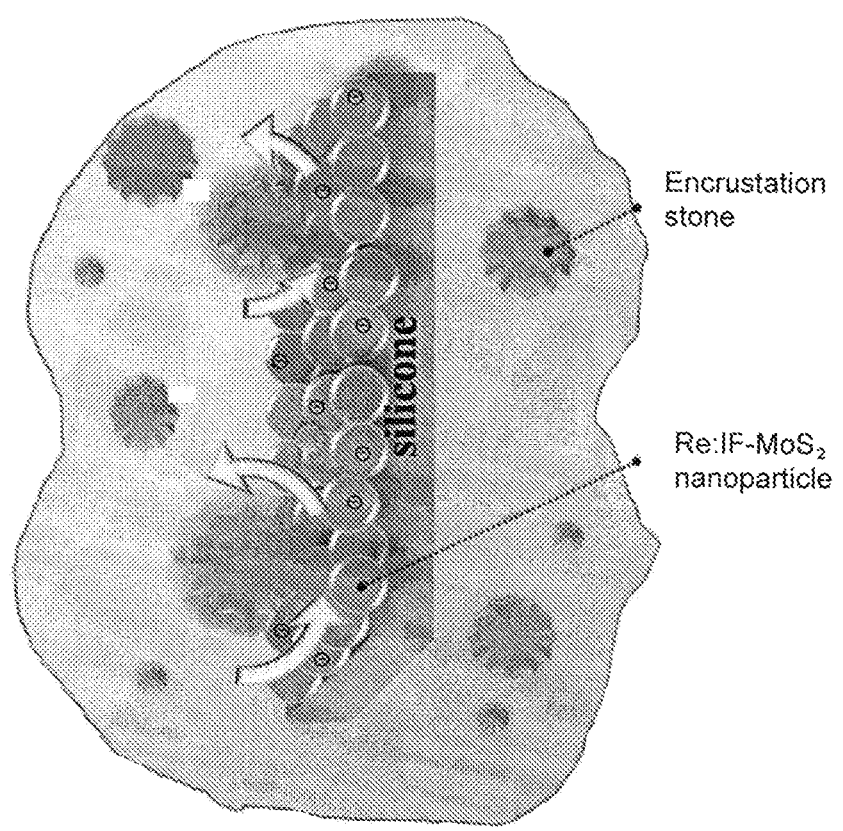
FIG. 11 is a schematic illustration of a catheter surface which is coated by the Re:IF—$MoS_2$ nanoparticles, in a urine environment under encrustation conditions. By self-assembly, the negatively charges nanoparticles produce a surface architecture which is close-packed and nano-bumped, with an arrangement resembles a mosaic pavement. Thus, encrustation stone are believed to slip from the surface as approaching it. This architecture, together with the low-affinity of the nanoparticles towards environment (closed-caged moieties which lack dandling bonds), their low surface energy and their superior lubrication behavior (low friction)—are all significantly difficult stones anchoring to the surface.

Additionally, due to its atomically smooth surface and low surface energy, the Re:IF—MoS$_2$ material is known to be chemically very inert and induce very low friction. Therefore, the anchoring potential of the hydroxyapatite colloidal nanoparticles to the underlying substrate is very low. Consequently, the stones are believed to "slip" on the Re:IF—MoS$_2$-coated catheters once approaching the surface (FIG. 11).

The visual absence of encrustation on bald areas at the Re:IF—MoS$_2$-coated catheter surfaces suggests that, even if some encrustation has occurred on these areas, these patches could be easily uprooted by the dynamic flow of the urine.

The specific structure and chemistry of each Re:IF—MoS$_2$ nanoparticle provides further support to the above model; The low surface energy (20 meV/Å2) of the basal (0001) 2H-MoS$_2$ surface, imply that the terminal (sulphur) atoms are very inert with respect to a specific chemical reaction in the present conditions. However, the curved (0001) surfaces of the IF-MoS$_2$ nanoparticles contain a small amount (<5%) of structural defects, which are chemically reactive, but can be passivated via adsorption of specific moieties. Such defects can be the source of the rather rare and random growth of stones on the surface coated catheters.

Materials and Methods

Coating Catheter Specimens by Re:IF—MoS$_2$ Nanoparticles—I

Specimens of a commercially all-silicone medical-grade 2-ways Foley catheter (Hangzhou Fushan Medical Appliances Co. Ltd., China. Supplied by: J.S Gull Ltd., Israel), French size (7.3 mm) and 400 mm long were employed throughout all the described experiments. Segments of 3 cm long were cut from the cylindrical shaft of the device and then were cut along the longitudinal axis. The external (convex) surfaces of the catheter specimens were used for carrying out all the reported analyses.

A suspension of 0.05 wt % Re:IF—MoS$_2$ nanoparticles in ultrapure H$_2$O (Milli-Q RG, Millipore) was sonicated, using an ultra-sonic probe mixer (Vibra Cell VCX400, 400 W, Sonics & Materials) for 30 min. The ultra-sonication was alternately applied (6 s activation, 4 s deactivation) on the Re:IF—MoS$_2$-suspension, during which a constant magnetic stirring was implemented.

Catheter specimens were individually suspended in vials contained 10 ml of the Re:IF—MoS$_2$ suspension. The vials were left 24 hours for mixing using a rotation machine. Prior to the analyses, the catheter specimens were removed from the Re:IF—MoS$_2$-suspension and were rinsed with ultrapure H$_2$O. Moreover, for the sake of comparison, uncoated bare catheter specimens were put inside similar vials which contained 10 ml H$_2$O, and were treated through the same procedure. Additional series of samples were prepared from pristine silicone catheters for reference purposes. These samples were analyzed without any prior treatment.

One way to prepare specifically adsorbed Re:IF—$MoS_2$ was to spread them in Langmuir-Blodgett (LB) trough and apply a surface pressure to condense them as 2D film of the nanoparticles on the solvent surface. The solvent could be in the form of an aqueous solution or a water-ethanol mixture in an acidic pH close to the isoelectric point (IEP). The surface layer was either sprayed from above with the silicone monomer and transferred to the catheter surface by careful immersion of the catheter and slow rotation to allow full coverage of the surface. Another possibility was to add to the solution chloroauric acid and a reducing agent, such as sucrose or hydrazine hydrate, which could be activated by light (<50° C.) heating. A Janus IF-gold nanoparticle 2D film is formed, which can then be functionalized with amine or thiol group silicone compound. This allows tethering the nanoparticles to the catheter surface with their upper face exposed to the urine solution. Other chemistries, like the use of $Fe_3O_4$ nanoparticles could also be thought (see J. K. Sahoo et al. Angew. Chem. Int. Ed. 2011, 50, 12271-12275).

Coating Catheter Specimens by Re:IF—$MoS_2$ Nanoparticles—II

In an alternative treatment, catheter specimens were coated by a direct application of horn-sonication into a solution of the Re:IF—$MoS_2$ NPs. First, a solution of (0.05 wt %) Re:IF—$MoS_2$ NPs in double-distilled water (Milli-Q RG, Millipore) was sonicated, using an ultra-sonic probe mixer (Vibra Cell VCX400, 400 W, Sonics & Materials Inc.) for 30 min. The sonication was alternately applied (6 s activation, 4 s deactivation of the horn) on the Re:IF—$MoS_2$-suspension, during which a constant magnetic stirring was implemented. Then, catheter specimens were added into the solution an sonication was applied for 10 min (5 s activation, 5 s deactivation) and after 5 min off, sonication was applied for another 8 min as before.

Coating Catheter Specimens by Re:IF—$MoS_2$ Nanoparticles—III

In another alternative treatment, catheter specimens were coated by dipping in a mixture of the Re:IF—$MoS_2$ NPs with a commercial medical-grade silicone rubber (0.05 wt %). The one-component primer-less RTV transparent silicone rubber using as a biomedical liquid glue and cures at ambient conditions (i.e. utilizing the water molecules in the humid air).

In-Vitro Encrustation Process

A simulated body encrustation process was conducted using a custom-built model of a catheterized-like urinary tract. The process was designated to imitate the circumstances in the urinary tract once it is under device-related infection conditions. This simulated stress results in precipitation of in-vivo-like encrustation deposits under defined, controlled and reproducible conditions. However, the incubation time-period in this study is much shorter and the rate of incidence of encrustation is much accelerated in comparison to the human-body. As was already pointed out, there exists no single standard for in-vitro test model for such experiments. Thus, a variety of models were reported introducing different fundamental experimental parameters, such as the urine source (human or artificial) and the infection source (live microorganisms or a synthetic agent to mimic the microorganisms' effect).

In the present work, the encrustation processes were performed in a glass reaction vessel equipped with a fitting lid within which 12 marked stainless steel rods were equally positioned. At the end of each rod stood a hook on which a single vertical specimen was positioned. The vessel was placed in an incubator to maintain the physiological temperature (37° C.). In order to systematically reproduce the conditions of the encrustation process along the experiments, an artificial urine solution was used. This solution has a well-defined composition, compared to the human urine which has a non-uniform composition among different native donors and within different micturitions of an individual donor. The solution consisted of 10 solutes (Table 4, initial pH=6.4-6.5), which concentrations were equivalent to the average concentration found over a 24 hours period in the urine of normal human Alkalinization of the urinal medium was triggered here by a direct addition of a Jack-bean-derived urease (type III, Sigma-Aldrich).

TABLE 4

The composition of the synthetic urine.

| Compound | Chemical formula | Concentration [g/L] |
|---|---|---|
| Calcium chloride | $CaCl_2 \cdot 2H_2O$ | 0.49 |
| Magnesium chloride hexahydrate | $MgCl_2 \cdot 6H_2O$ | 0.65 |
| Sodium chloride | NaCl | 4.6 |
| Di-sodium sulphate | $Na_2SO_4$ | 2.3 |
| Tri-sodium citrate dihydrate | $HOC(COONa)(CH_2COONa)_2 \cdot 2H_2O$ | 0.65 |
| Di-sodium oxalate | $Na_2C_2O_4$ | 0.02 |
| Potassium dihydrogen phosphate | $KH_2PO_4$ | 2.8 |
| Potassium chloride | KCl | 1.6 |
| Ammonium chloride | $NH_4Cl$ | 1.0 |
| Urea | $NH_2-CO-NH_2$ | 25 |

The urease was supplied as a lyophilized powder, which was dissolved in a pre-prepared filtered (0.45 μm) sodium phosphate buffer (2 M, pH=7.0). In most of the reported experiments, the urease concentrations and incubation times were approx. 0.05 mg per 100 ml (5 ppm) urine solution and approximately 8-12 hours, respectively. The enzyme powder was found to be very hygroscopic, affecting the actual enzyme solution concentrations. Therefore, it is important to emphasize that the incubation period, i.e. the time lapse for turbidity varied somewhat from one series of measurement to the other, pending on the freshness of the enzyme powder which is very hygroscopic. Thus, care was taken to maintain the enzyme in strictly dry conditions. Furthermore, during all sets of experiments, the two kinds of specimens (Re: IF—$MoS_2$-coated and uncoated) were simultaneously incubated in the encrustation reactor. The samples were taken out for analysis as soon as the solution lost its full transparency and became massively turbid. Upon removal of the encrusted specimens out of the in-vitro model, they were gently rinsed with ultrapure $H_2O$ to remove loosely attached debris and were stored inside an evacuated desiccator till further analyses. Furthermore, along each experiment pH measurements were carried out by a pH-meter (pH510, Eutech instruments).

SEM and EDS Analyses

SEM (model Ultra 55 FEG Zeiss; LEO model Supra 55 vp, Carl Zeiss International, Oberkochen, Germany, and E-SEM-FEG XL30 Philips/FEI) were used for this study. The SEM set-ups were operated in either SE or BSE modes.

EDS (EDAX instrument Phoenix, attached to the E-SEM), was used for the chemical analysis of the specimens. Here, two modes of work were implemented for the chemical analysis. In the first one, the beam was focused on a single stone (high magnification). The analysis was repeated three times for stones of the same morphology and the result is reported as an average of the three measurements. In addition, a global (low magnification) EDS analysis of the encrusted surface (3000 $\mu m^2$) was carried out. The EDS analysis of bare; encrusted uncoated and Re:IF—$MoS_2$-coated catheter specimens were compared. All the low magnification EDS analyses were performed by sampling three distinct surface locations. The results are reported as average of the three EDS measurements. The accelerating voltage of the beam for the EDS analysis was limited to 15 keV.

SEM imaging and image analysis were used to obtain quantitative analysis of the encrustation developed on the catheter surface. Imaging the catheter surface with the SE detector proved to be rather problematic for this purpose. Discrimination between the precipitated stones and the Re:IF—$MoS_2$ nanoparticles was effective under high magnification (×20,000), only. However, the heterogeneity of the surface did not permit acquiring sufficient data for a fully quantitative analysis under high magnification. Conversely, at low magnifications the discrimination between the stones and the Re:IF—$MoS_2$ nanoparticles was not adequate in the SE mode. Therefore, mapping the encrusted surface with BSE detector, which is sensitive to the atomic number (Z) combined with image analysis was preferred for the quantitative analysis. The contrast difference in the BSE mode allowed clear discrimination between the encrusted stones, the Re:IF—$MoS_2$ nanoparticles and the substrate in lower magnifications (×5000) and over large surface areas, thus enabling quantitative analysis of the different substrates.

Confirmation of the BSE mapping with EDS analysis, which is slow and rather tedious, was done with full agreement between the two analyses. The surface area of an Re:IF—$MoS_2$ nanoparticles-coated specimen after encrustation was analyzed by dividing the surface into a raster (mesh). Each raster unit was scanned by the BSE detector in a magnification of ×5,000 (50 micrographs, 640 $\mu m2$ each, 32,000 $\mu m^2$ total area). Image analysis of the BSE data was done using the ImageJ (National Institutes of Health, USA) software.

Samples for the SEM analyses were prepared in the following manner; ~5×5 $mm^2$ samples were cut from the middle of each parent sample. A thin layer of gold-palladium was evaporated on each specimen using a high vacuum evaporation set-up (S150 sputter coater, Edwards). For the EDS analysis, carbon evaporation was applied instead, using a high vacuum evaporation set-up (BOC FL400, Edwards).

XPS Measurements

The XPS measurements were carried-out with Kratos AXIS ULTRA system, operating at ultra-high (10-9 torr) vacuum. A monocromatized Al (Kα) X-ray source (hv=1486.6 eV) at 75 W and detection pass energies ranging between 40 and 80 eV were used. The data was recorded at a take-off angle of 0° with respect to the surface normal. Low-energy electron flood gun (eFG) was applied for charge neutralization. The binding energy scale was referenced to the main C (1s) peak attributable to hydrocarbon at 284.9 eV.

To minimize the beam damage effects, the analysis time was 30 min Curve fitting analysis was based on linear background subtraction and application of Gaussian-Lorenzian line shapes. Quantification was carried-out using the peak area, and corrected with Scofield sensitivity factors. Signals were collected from area size of 900×400 $\mu m^2$ for each sample.

In addition to the encrusted specimens, a few non-encrusted samples (prior to urine exposure) for control were also analyzed including: Re:IF—$MoS_2$-coated and also bare untreated catheter specimens.

XRD Measurements

The XRD measurements were carried out in reflection geometry using a diffractometer (TTRAX III Rigaku, Japan) equipped with a rotating Cu anode operating at 50 kV and 200 mA and with a scintillation detector. θ/2θ scans were performed at specular conditions in Bragg-Brentano mode with variable slits. The samples were scanned from 5 to 50 degrees of 2θ with step size of 0.025 degrees and scan speed of 0.4 degree per minute. Phase analysis was made using the Jade 9.1 software (Materials Data, Inc.) and PDF-4+ 2010 database (ICDD).

The invention claimed is:

1. An implantable or insertable medical device in a body of a subject, coated on at least one surface region thereof with a non-adherent film, said film consisting of inorganic nanoparticles, wherein the inorganic nanoparticles are inorganic fullerene-like nanoparticles (IF nanoparticles), or inorganic nanotubes (INT), wherein the inorganic nanoparticles being of the general formula $A_{1-x}$-$B_x$-chalcogenide, wherein A is a metal or a transition metal or an alloy of such a metal/transition metal, B is a metal or a transition metal, and x being ≤0.3 and different from zero, provided that: A≈B; wherein said film comprises domains displaying self-assembly of said nanoparticles into closed-packed arrays with a mosaic appearance, wherein said surface is made of silicones or plastics; wherein said inorganic nanoparticles are attached directly to the device surface; wherein said film does not comprise a coating matrix or a coating composite substrate in which the nanoparticles are embedded; and wherein said at least one surface region of the device is intended for direct contact with at least one inner-body tissue of a subject's body.

2. The medical device of claim 1, being selected amongst devices used in diagnosis or in a medical procedure and which residence in the subject's body of the patient increases susceptibility to growth and attachment of adventitious materials or exudates, or to result in the formation of biofilms.

3. The medical device of claim 1, being a device used in diagnosis or treatment of any pathological and non-pathological condition.

4. The medical device according to claim 3, wherein said condition is associated with a tissue, a gland, a tumor, a cyst, a muscle, a fascia, a skin region, an adipose, a mucous membrane, or any one organ being damaged or diseased, enlarged beyond its normal size, or stretched, obstructed, occluded, or collapsed of or from an adjacent body lumen or anatomical structure.

5. The medical device of claim 1, for bridging between two or more body organs, lumens or tissues.

6. The medical device of claim 1, being implanted for periods of between days and months to years in a recipient.

7. The medical device of claim 1, the medical device being an endoprosthesis.

8. The medical device according to claim 7, being selected from stents; catheters; dialysis tubes; cannulas; and sutures.

9. The medical device of claim 1, the medical device being a hollow device for inserting through a body opening or through the skin into a body cavity, duct, or vessel.

10. The medical device of claim 1, the medical device being a ureteral or urethral stent or catheter.

11. The medical device according to claim 1, wherein x is 0.01, or below 0.005.

12. The medical device according to claim 11, wherein x is between 0.005 and 0.01.

13. The medical device according to claim 1, wherein A is a metal or transition metal or an alloy of metals or transition metals selected from Mo, W, Re, Ti, Zr, Hf, Nb, Ta, Pt, Ru, Rh, In, Ga, WMo, and TiW.

14. The medical device according to claim 1, wherein B is a metal or transition metal selected from Si, Nb, Ta, W, Mo, Sc, Y, La, Hf, Ir, Mn, Ru, Re, Os, V, Au, Rh, Pd, Cr, Co, Fe and Ni.

15. The medical device according to claim 13, wherein the nanoparticles are selected from $WS_2$ and $MoS_2$ and are doped with Re or Nb.

16. The medical device according to claim 13, wherein the metal chalcogenide nanostructures of the formula $A_{1-x}B_x$-chalcogenide are selected from $W_{1-x}B_x$-chalcogenide, $Mo_{1-x}B_x$-chalcogenide, $Nb_{1-x}B_x$-chalcogenide and $Ta_{1-x}B_x$-chalcogenide.

17. The medical device according to claim 16, wherein the nanoparticles are doped with dopant atoms B selected from atoms Si, Nb, Ta, W, Mo, Sc, Y, La, Hf, Ir, Mn, Ru, Re, Os, V, Au, Rh, Pd, Cr, Co, Fe and Ni.

18. The medical device of claim 1, wherein said device is produced by a process comprising:
forming a suspension or a solution comprising at least one solvent such that:
said suspension or solution comprising the inorganic fullerene-like nanoparticles (IF nanoparticles) or inorganic nanotubes (INT) within said at least one solvent; or
said suspension or a solution comprising said inorganic fullerene-like nanoparticles nanoparticles) or inorganic nanotubes (INT) as a 2D film on the solvent surface; or
a combination thereof
dipping the medical device in said solution/suspension or bringing the medical device into contact with said solution/suspension;
optionally mixing/sonicating said solution/suspension;
thus forming a film of inorganic fullerene-like nanoparticles (IF nanoparticles) or of inorganic nanotubes (INT) comprises domains displaying closed-packed arrays with a mosaic appearance on said surface.

19. An implantable medical device or an insertable medical device in a body of a subject configured to be implanted in a subject, the device comprising an implantable unit or structure, wherein at least a surface region of said unit or structure being coated with a non-adherent film of inorganic nanoparticles, wherein the inorganic nanoparticles are inorganic fullerene-like nanoparticles (IF-nanoparticles) or inorganic nanotubes (INT) adapted to prevent or inhibit deposition of encrustation and/or formation of a biofilm thereon after implantation in the subject; wherein said film comprises domains displaying self-assembly of said nanoparticles into closed-packed arrays with a mosaic appearance wherein said surface is made of silicones or plastics; wherein the inorganic nanoparticles being of the general formula $A_{1-x}$-$B_x$-chalcogenide, wherein A is a metal or a transition metal or an alloy of such a metal/transition metal, B is a metal or a transition metal, and x being ≤0.3 and different from zero, provided that: A≉B, wherein said inorganic nanoparticles are attached directly to the device surface; and wherein said film does not comprise a coating matrix or a coating composite substrate in which the nanoparticles are embedded.

20. The medical device of claim 19, wherein said device is produced by a process comprising:
forming a suspension or a solution comprising at least one solvent such that:
said suspension or solution comprising the inorganic fullerene-like nanoparticles (IF nanoparticles) or the inorganic nanotubes (INT) within said at least one solvent; or
said suspension or a solution comprising the inorganic fullerene-like nanoparticles nanoparticles) or inorganic nanotubes (INT) as a 2D film on the solvent surface; or
a combination thereof;
dipping the medical device in said solution/suspension or bringing the medical device into contact with said solution/suspension;
optionally mixing/sonicating said solution/suspension;
thus forming a film of IF nanoparticles or of inorganic nanotubes (INT), said film comprises domains displaying closed-packed arrays with a mosaic appearance on said surface.

21. A process for reducing, diminishing or preventing the formation of encrustations on a surface region of an implantable medical device or insertable medical device in a body of a subject, the process comprising forming a non-adherent coating or a film of inorganic nanoparticles, wherein the inorganic nanoparticles are inorganic fullerene-like nanoparticles (IF-nanoparticles) or inorganic nanotubes (INT) on said surface region prior to implanting or inserting said device into a body tissue, organ or body lumen, wherein said film comprises domains displaying self-assembly of said nanoparticles into closed-packed arrays with a mosaic appearance, wherein said surface is made of silicones or plastics; and wherein the inorganic nanoparticles being of the general formula $A_{1-x}$-$B_x$-chalcogenide, wherein A is a metal or a transition metal or an alloy of such a metal/transition metal, B is a metal or a transition metal, and x being ≤0.3 and different from zero, provided that: A≉B, wherein said inorganic nanoparticles are attached directly to the device surface; and wherein said film does not comprise a coating matrix or a coating composite substrate in which the nanoparticles are embedded.

* * * * *